(12) United States Patent
Howell

(10) Patent No.: US 6,254,604 B1
(45) Date of Patent: Jul. 3, 2001

(54) TIBIAL GUIDE

(75) Inventor: Stephen M. Howell, Elk Grove, CA (US)

(73) Assignee: Arthrotek, Inc., Warsaw, IN (US)

(*) Notice: Subject to any disclaimer, the term of this patent is extended or adjusted under 35 U.S.C. 154(b) by 0 days.

(21) Appl. No.: 09/300,680

(22) Filed: Apr. 27, 1999

Related U.S. Application Data

(63) Continuation-in-part of application No. 08/494,019, filed on Jun. 23, 1995, now Pat. No. 6,019,767, which is a continuation-in-part of application No. 08/222,082, filed on Apr. 4, 1994, now Pat. No. 5,570,706, which is a division of application No. 08/020,901, filed on Feb. 23, 1993, now Pat. No. 5,300,077, which is a continuation of application No. 07/552,815, filed on Jul. 16, 1990, now abandoned.

(51) Int. Cl.[7] .................................................. A61B 17/17
(52) U.S. Cl. .............................................. 606/96; 606/88
(58) Field of Search .................................. 606/88, 89, 96, 606/97, 98, 102, 104; 623/13

(56) References Cited

U.S. PATENT DOCUMENTS

| | | |
|---|---|---|
| 4,257,411 | 3/1981 | Cho . |
| 4,301,551 | 11/1981 | Dore et al. . |
| 4,467,478 | 8/1984 | Jurgutis . |
| 4,483,023 | 11/1984 | Hoffman et al. . |
| 4,541,424 | 9/1985 | Grosse et al. . |
| 4,566,466 | 1/1986 | Ripple et al. . |
| 4,590,928 | 5/1986 | Hunt et al. . |
| 4,605,414 | 8/1986 | Czajka . |
| 4,708,139 | 11/1987 | Dunbar, IV . |
| 4,712,542 | 12/1987 | Daniel et al. . |
| 4,739,751 | 4/1988 | Sapega et al. . |
| 4,781,182 | 11/1988 | Purnell et al. . |
| 4,787,377 | 11/1988 | Laboureau . |
| 4,823,780 | 4/1989 | Odensten et al. . |
| 4,883,048 | 11/1989 | Purnell et al. . |
| 4,901,711 | 2/1990 | Goble et al. . |
| 4,911,153 | 3/1990 | Border . |
| 4,920,958 | 5/1990 | Walt et al. . |
| 4,945,904 | 8/1990 | Bolton et al. . |
| 4,997,433 | 3/1991 | Goble et al. . |

(List continued on next page.)

FOREIGN PATENT DOCUMENTS

| | | |
|---|---|---|
| 2 747 568 | 4/1979 | (DE) . |
| 3 507 80A1 | 1/1990 | (EP) . |
| WO 9400058 | 1/1994 | (EP) . |
| 1 448 111 | 9/1976 | (GB) . |
| 858799 | 8/1891 | (SU) . |

OTHER PUBLICATIONS

"Customized Tibial Tunnel Placement: Why The Surgeon Should Consider this Technique" brochure published by Arthrotek, 1994.
"Impingement–Free Tibial Guide System Surgical Technique" brochure published by Arthotek, 1992.
Declaration of Stephen M. Howell with two attached brochures of Acufex Microsurgical, Inc., entitled "Endoscopic Technique for ACL Reconstruction With Pro–Trac Tibial Guide: Endobutton Fixation" and "Techniques for ACL Reconstruction With Multi–Trac™ Drill Guide".

*Primary Examiner*—David O. Reip
(74) *Attorney, Agent, or Firm*—Harness, Dickey & Pierce, P.L.C.

(57) ABSTRACT

A drill guide for determining the site for and drilling a tunnel in a tibia during an anterior cruciate ligament replacement procedure and method for using same are also disclosed. The drill guide utilizes a multiple-point anatomical reference system for determining the most favorable position for the tibial tunnel, based on isometry, freedom from impingement and desired ACL-PCL interaction. The drill guide further utilizes a removable guide bar to provide visual alignment of the drill guide relative to the coronal plane of the knee joint.

14 Claims, 16 Drawing Sheets

U.S. PATENT DOCUMENTS

| | | |
|---|---|---|
| 5,112,335 | 5/1992 | Laboureau et al. . |
| 5,112,337 | 5/1992 | Paulos et al. . |
| 5,139,520 | 8/1992 | Rosenberg . |
| 5,154,720 | 10/1992 | Trott et al. . |
| 5,163,940 | 11/1992 | Bourque . |
| 5,269,786 | 12/1993 | Morgan . |
| 5,300,077 | 4/1994 | Howell . |
| 5,320,626 | 6/1994 | Schmieding . |
| 5,324,296 | 6/1994 | Laboureau et al. . |
| 5,350,383 | 9/1994 | Schmieding et al. . |
| 5,409,494 | 4/1995 | Morgan . |
| 5,743,909 * | 4/1998 | Collette .................................. 606/88 |
| 5,968,050 | 10/1999 | Torrie . |

\* cited by examiner

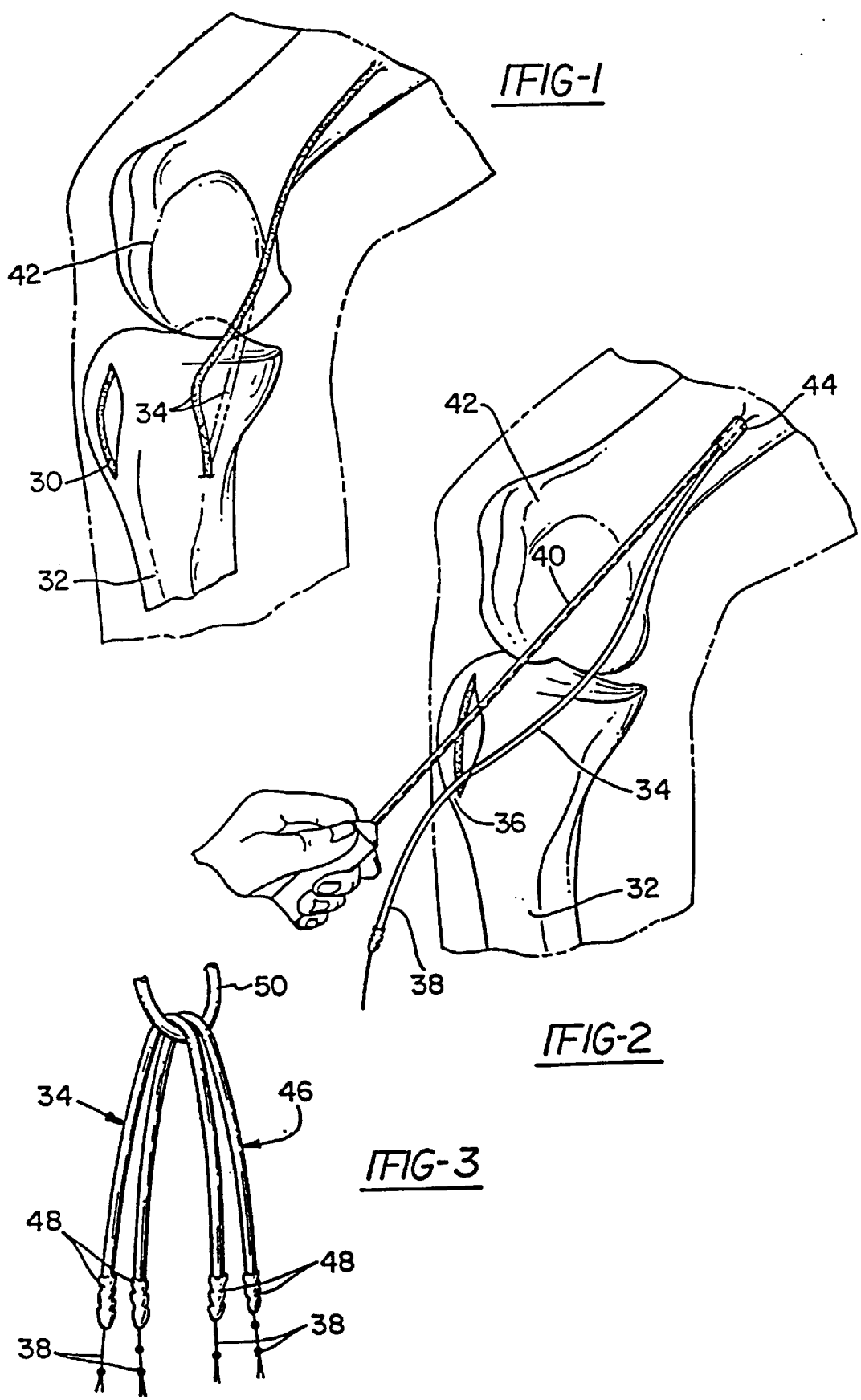

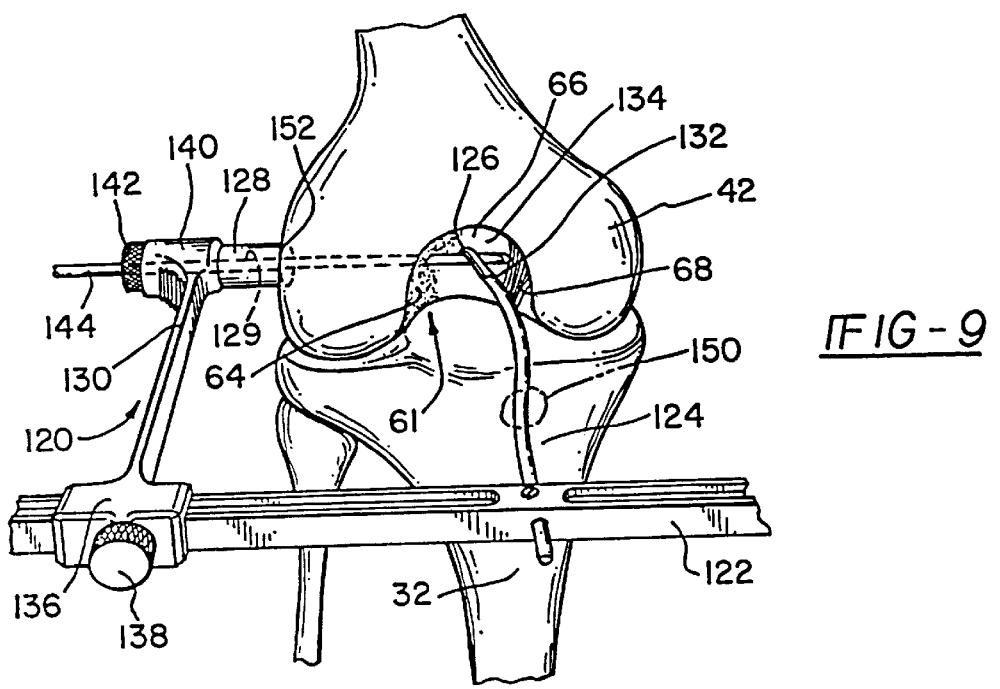

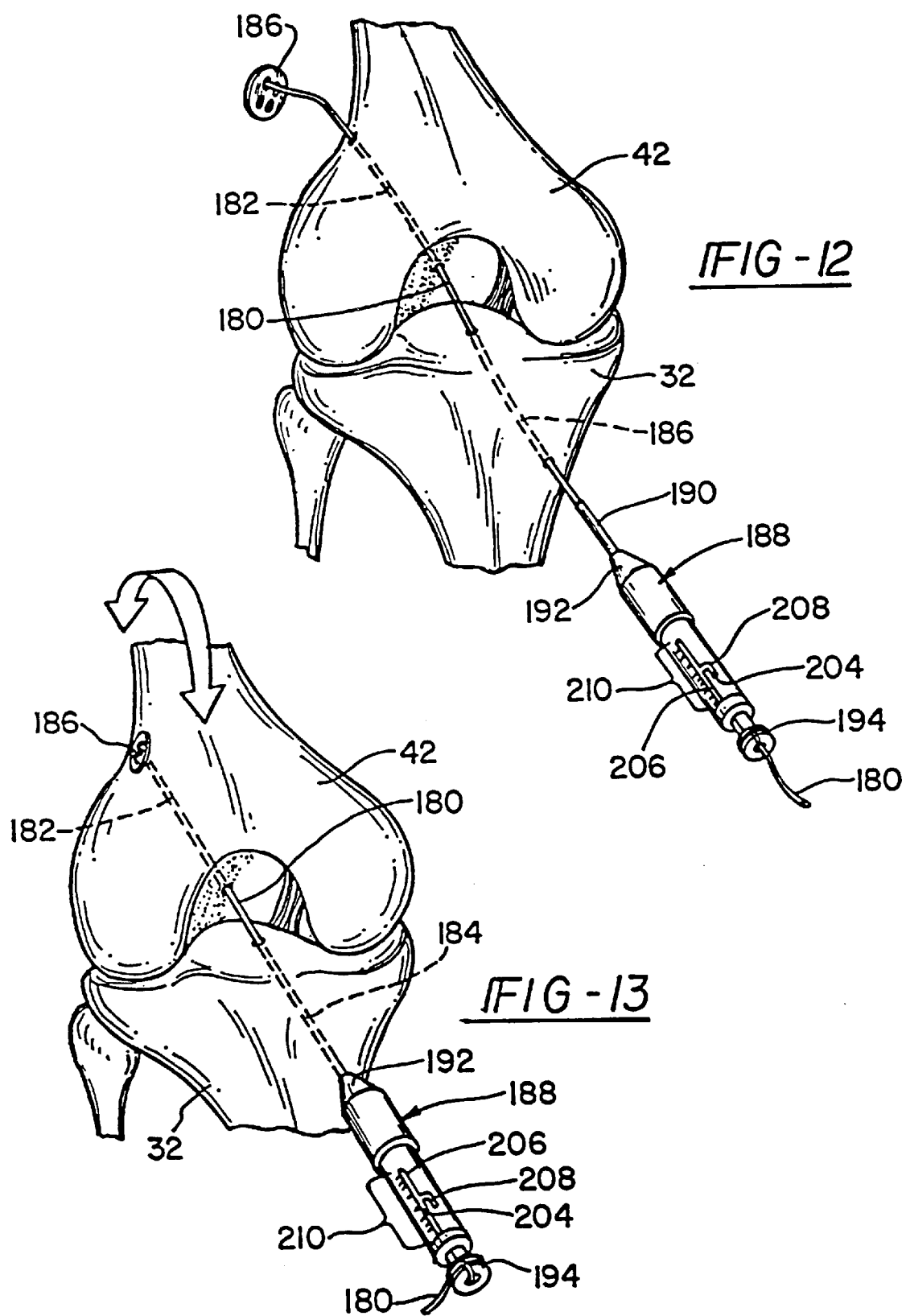

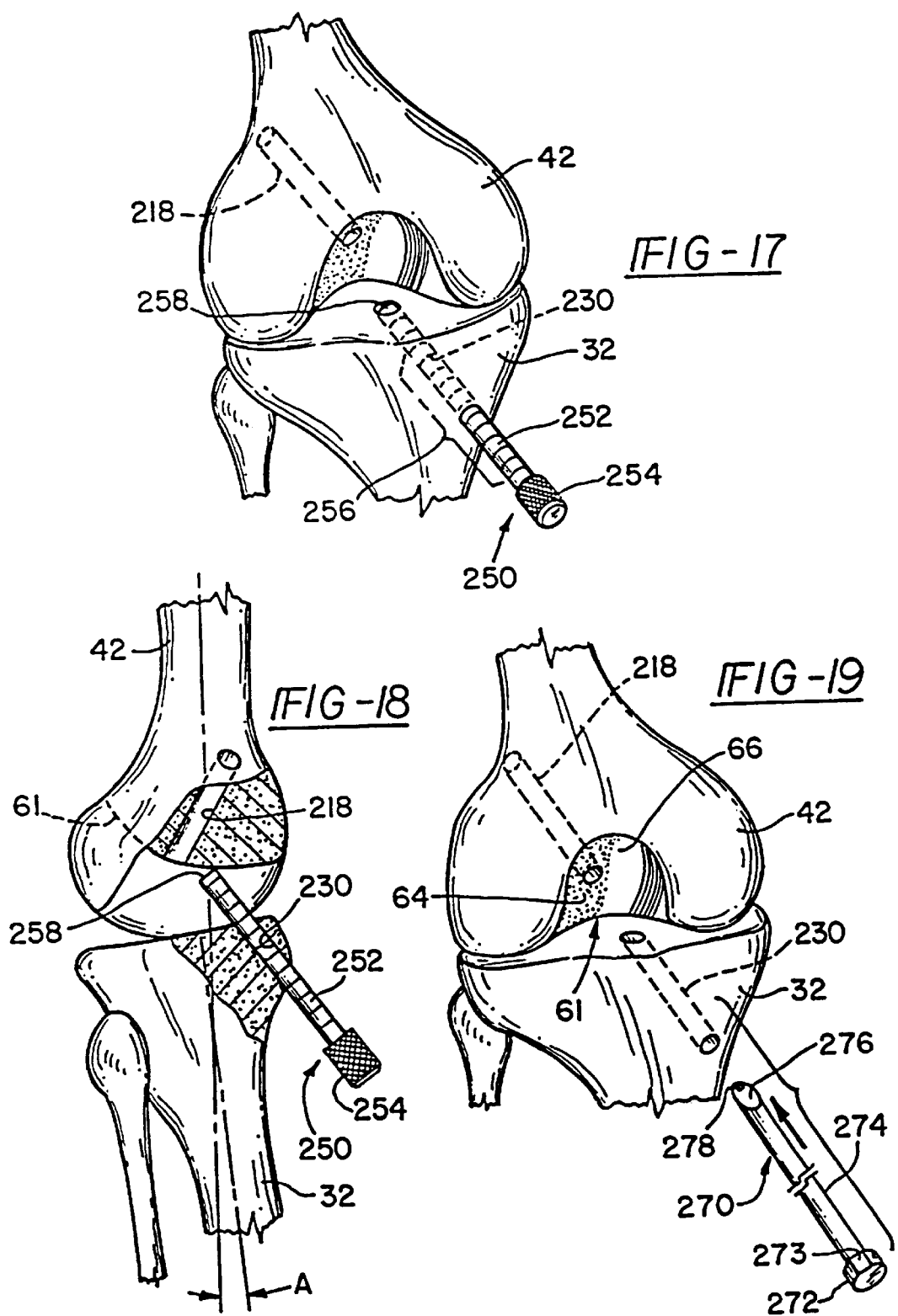

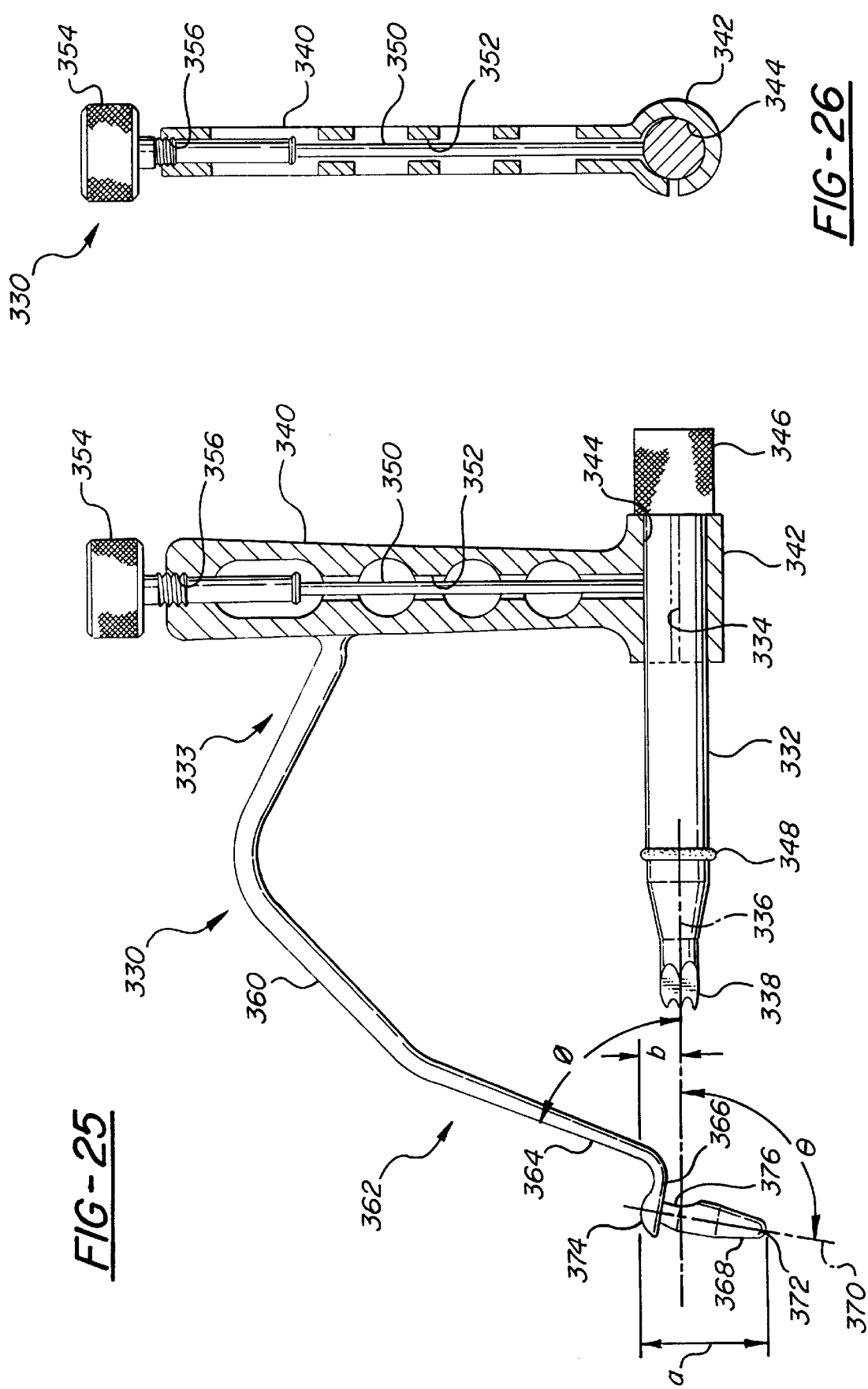

TIBIAL GUIDE

CROSS REFERENCE TO RELATED APPLICATIONS

This application is a continuation-in-part application of U.S. Ser. No. 08\494,019, filed Jun. 23, 1995, now U.S. Pat. No. 6,019,767, which is a continuation-in-part application of U.S. Ser. No. 08\222,082, filed Apr. 4, 1994, now U.S. Pat. No. 5,570,706, which is a divisional of U.S. Ser. No. 08\020,901, filed Feb. 23, 1993, now U.S. Pat. No. 5,300,077, which is a continuation of U.S. Ser. No. 07\552,815, filed Jul. 16, 1990, now abandoned.

TECHNICAL FIELD

The present invention relates to an improved method for reconstruction of a torn anterior cruciate ligament using endoscopic techniques, as well as new and improved instruments for use with the method. The present invention also relates to an improved drill guide device for drilling a tibial tunnel in the reconstruction of a torn anterior cruciate ligament using arthroscopic or endoscopic techniques, as well as a method for using this device.

BACKGROUND OF THE INVENTION

Most people today are involved in a sport or some other type of physical activity. Some of these activities involve a low risk chance of injury, such as walking and swimming, while others involve a high risk chance of injury, such as football and skiing.

Damaged ligaments, cartilage and tendons in joints are not an uncommon occurrence, particularly in some of these high risk activities and sports. One of the joints which requires particular skill and presents particular difficulties in repairing is the knee joint.

Numerous improvements in repairing damage to knee joints have been made over the years, and some of the major advances involve the use of endoscopic techniques and arthroscopic procedures. Arthroscopic surgery is particularly useful in excising or repairing damaged knee cartilage.

Endoscopic techniques have also been developed for use in repair and reconstruction of damaged anterior cruciate ligaments (ACL) and posterior cruciate ligaments (PCL). When the ACL in particular has ruptured and is non-repairable, it is usually replaced in young adults and the knee reconstructed through use of grafts (biological or synthetic). Some known methods and techniques which have been used to repair and replace ACL ruptures with grafts are discussed, for example, in Moore U.S. Pat. No. 4,773,417, Goble U.S. Pat. No. 4,772,286 and an article by Goble entitled "FLUO-ROARTHROSCOPIC ALLOGRAFT ANTERIOR CRUCIATE RECONSTRUCTION", Techniques Orthop. 1988 2(4): 65–73.

The function of the real cruciate ligaments is complicated. The ACL and PCL are three-dimensional structures with broad attachments and a continuum of fibers. These fibers are of different lengths, have different attachment sites, and are under different tensions. Although many current substitutes for cruciate ligaments have not duplicated the complex orientation and operation of normal ACLs, they operate the best and mimic the normal ACL operation the best when they are placed isometrically. "Isometrically" positioned means that the length of the substitute ligament will not change during angular movement of the tibia relative to the femur; the distance between the affixed ends of the ligament remains a constant. Isometric placement maximizes the number of fibers that can be taut throughout the range of motion of the knee and allows for early knee motion without generating high ligament strains.

Correct isometric positioning of the ACL graft is an important factor for a successful operation; isometrically placed grafts provide the most stable knees. Correct isometric placement reproduces corresponding femoral and tibial anatomic attachment sites and will allow an ACL graft to mimic the normal ACL. Non-isometric graft placement can result in plastic deformation of the ACL substitute, postoperative laxity, abnormal kinematics, or failure of fixation.

The importance of accurate placement of the graft tunnels and ACL substitute is shown by the fact that graft placements sometimes only several millimeters apart produce significantly different strains in the cruciate substitute. A placement of the ACL origin or insertion which is too anteriorly placed in the knee joint results in a ligament that is taut in flexion, but lax in extension. Posterior placement causes the ligament to be taut in extension, but lax in flexion. Only isometric tunnel placement provides stability throughout the range of motion. Therefore, one of the challenges during anterior cruciate ligament replacement procedures is the accurate isometric placement of the tibial tunnel. Another challenge during anterior cruciate ligament replacement is the accurate placement of the tibial tunnel relative to the longitudinal axis of the tibia. In this regard, it has been determined that the medial or lateral orientation of the tibial tunnel relative to the longitudinal axis of the tibia must also be taken into consideration.

The preparation of the intercondylar notch is also important as is the proper positioning and placement of the femoral and tibial tunnels. Accurate and sufficient notchplasty prevents impingement of the graft which could cause failure or significant complications. Often today the amount and degree of notchplasty is determined during an operation by "feel" or experience. This frequently results in more of the bone in the notch being removed than is necessary, or in less of the bone being removed than is required necessitating later correction in the operation.

U.S. Pat. No. 5,300,077 to Howell, the inventor herein, discloses methods and instruments for ACL reconstruction. Many of the method steps disclosed therein for replacement of an ACL are substantially utilized herein. However, the drill guide and method for using according to the present invention represent improvements in that portion of the procedure surrounding the formation of the tibial tunnel for an ACL graft.

Additionally, reconstructed knees typically regain more extension, have less pain and exhibit better stability when anterior cruciate ligament grafts are placed without femoral roof impingement. This is true, at least in part, because impingement of an ACL upon the femoral roof causes flexion contractures because the graft constrains the knee as a mechanical stop. If abrasion progresses to involve all the fibers of the graft, then the graft can fail, resulting in recurrent instability of the knee. To avoid flexion contractures and recurrent instability caused by roof impingement, the tibial tunnel should be positioned posterior and parallel to the slope of the intercondylar roof with the knee in full extension.

Another related challenge in the ACL replacement procedure is to minimize the amount of bone removed from the femoral intercondylar roof to prevent impingement during extension. Correct placement of the tibial tunnel prevents abrasive wear between the ACL graft and the intercondylar roof while minimizing the extent of roofplasty required to avoid impingement. This results in time and effort savings, and maximizes the desirable feature of preserving the maximum amount of natural bone in the knee. It is another goal of ACL replacement procedures to create tibial tunnel placement that may allow the implanted ACL to interact more normally with the PCL.

Standard tibial drill guides place the tibial tunnel in the same relative position for each patient. The most favorable position is often determined using these devices with reference to a single point on one of the bone surfaces in the knee joint region. This single reference point may be a tibial surface such as the PCL, the ACL stump or another point of reference. The determination of a favorable tunnel position may also involve the use of pins or other ancillary guide devices used in connection with the main device used for guiding the procedure. The use of such additional devices may cause these procedures to be more time-consuming and involve a greater amount of effort on the part of the surgeon. They may also require a greater number of surgical incisions for their insertion, and/or may require the use of two hands or more than one person for their manipulation.

In practice, however, different patients have different anatomies pertinent to formation of the tibial tunnel. The differences in these anatomies often occur in more than a one-dimensional context. For example, the degree of knee extension and the slope of the femoral intercondylar roof vary widely between knees. Therefore, the optimum location for the tibial tunnel, with regard to isometry, minimizing impingement and allowing proper interaction with the PCL may vary among patients in more than a one-dimensional context. Because use of a single reference point places the tibial tunnel at the same relative location for each patient, a multiple reference point system that takes several surfaces into account can provide superior determination of the optimum tibial tunnel location.

It is an object of the present invention to provide an improved method using endoscopic/arthroscopic techniques for reconstruction of ACLs. It is a further object to provide isometric placements of ACL substitutes, and isometric placements which are objectively accurate and reproducible.

It is also an object of the invention to insure against impingement of the ACL substitute/graft in the joint. It is another object of the invention to provide a system for accurately determining whether notchplasty needs to be performed in the intercondylar notch to prevent impingement, and then performing the necessary notchplasty.

It is still a further object of the invention to provide an ACL replacement which is minimally invasive in order to minimize trauma and facilitate faster patient healing and rehabilitation. It is another object to provide a method of ACL reconstruction which preferably uses biological grafts from the patient.

Further objects of the invention include development and use of improved instruments for ACL operations which help assure accurate and sufficient notchplasty of the intercondylar notch, and provide an improved method for ACL reconstruction.

It is therefore advantageous to develop an instrument for ACL replacement procedures, and a method for using, that determines custom placement of the tibial graft tunnel, for maximizing isometry, minimizing graft impingement and allowing proper ACL-PCL interaction. It is also advantageous to develop an instrument that is convenient and quick to use, that minimizes effort required by the surgeon and reduces the number of ancillary devices required.

SUMMARY OF THE INVENTION

The above and other objects of the invention are met by the inventive method of ACL reconstruction and instrumentation which are disclosed and claimed in this application.

For the improved method, the knee joint is examined to confirm the rupture. The patient is anesthetized and the surgical site prepped and draped. The gracilis and semitendinosus tendons are harvested from the patient for use as the graft (or another type of ACL substitute is obtained). The graft is prepared for later implantation. Sutures are stitched at the free ends of the tendons for use in grasping and handling them and the tendons are double-looped forming a composite graft. The size of the graft is measured in order to select the proper drill/reamer size for the osseous tunnels.

The knee is examined by arthroscopic procedures and any observed minor defects or irregularities are taken care of. The lateral wall of the intercondylar notch is debrided and sculptured (i.e. "wallplasty"). Both manual and powered instruments can be used for this purpose. The torn ACL stump is removed from the intercondylar notch and the joint is cleaned.

The femoral attachment site for the ACL graft is determined visually and marked with a small recess by a curette. The femoral lateral cortex is exposed and a rear entry drill guide is utilized to drill a small hole through the femur to the recess.

A unique transverse drill guide is used to position and place a locator pin transversely through the femur. The transverse drill guide has an elongated slide bar, a bent wire aimer with a curved tip, a drill sleeve and a drill sleeve positioning member. The aimer has a groove which is adapted to nest with the intercondylar notch in order to accurately position it in place. Once the aimer and attached slide bar are positioned in place, the positioning member slides on the slide bar and positions the drill sleeve in the proper position. The transverse locator pin is drilled through the drill sleeve and passes through the intercondylar notch adjacent the curved tip of the aimer.

The transverse locator pin is used to position a unique anterior tibial drill guide which in turn is used to drill a small hole through the intercondylar roof with the knee in hyperextension. The anterior tibial drill guide utilizes the same drill sleeve positioning member as the transverse drill guide and also includes an elongated slide bar and bent wire hook. The curved tip of the bent wire hook is hooked over the femoral transverse locator pin and the top of the bent wire hook is positioned against the roof of the intercondylar notch. A small hole is drilled in the tibia through a drill sleeve situated in the positioning member on the slide bar.

The small holes in the femur and tibia preferably are then checked isometrically to determine if they are the proper sites for the osseous tunnels for the ACL graft. A suture passed through the two holes is secured to a button on the lateral femoral cortex and passed through and secured to a tensiometer on the tibia. The tensiometer is unlocked and readings are taken during movement of the knee.

If the proposed site is isometric, then the femoral and tibial tunnels are drilled. Guide pins are positioned in the two tunnels and the tunnels are drilled using cannulated drills or reamers placed over the pins. The inner edges of the tunnels are smoothed and chamfered.

The possible impingement of the roof of the intercondylar notch on the substitute ACL graft is then checked. A calibrated sizer is passed through the tibial tunnel and any impingement noted. If any impingement is determined, it is marked with a unique gouge instrument and a roofplasty is performed. The sizer is reused and the knee analyzed again until all of the impingement has been eliminated.

The substitute ACL graft is then passed through the osseous tunnels and secured in place. The double-looped end of the graft is affixed to the lateral femoral cortex by a cancellous screw. Once the graft is pulled tightly into position and minimal movement of the graft during rotation of the knee is observed, the graft is affixed to the tibia by bone staples.

After the graft is fully secured in place and examined, the wounds around the knee are closed and dressed. A leg brace is installed and appropriate postoperative care is followed.

The present invention also provides a drill guide for determining the site for and drilling a tunnel in a tibia during an anterior cruciate ligament replacement procedure. The drill guide is suitable for use in arthroscopy as well as in open procedures. The drill guide utilizes a multiple-point anatomical reference system for determining the most favorable position for the tibial tunnel, based on isometry, freedom from impingement and desired ACL-PCL interaction. Preferably, the drill guide is configured in a specialized arrangement to determine isometry at three points of contact. These three points of contact are the trochlear groove, the femoral intercondylar roof and the tibial eminence. This drill guide enables a surgeon to prepare a customized tibial tunnel based upon each patient's unique anatomy, including femoral roof angle and degree of knee extension. Thus, tibial tunnel placement can properly vary from patient to patient.

The tibial drill guide includes a drill sleeve for determining the site for and drilling a tunnel in a tibia. The drill sleeve includes a drilling axis upon which a drilling procedure can be performed. The drill sleeve also includes an aperture suitable for allowing the passage of a drilling device, such as a K-wire or drill bit. The aperture preferably includes a longitudinal axis disposed upon the drilling axis. The tibial drill guide also includes a guide assembly attached to the drill sleeve. The guide assembly preferably includes an elongated positioning member, a guide arm and an extension located at an end of the guide arm. The guide arm and extension are contoured and arranged in a specific configuration. This allows the guide assembly to provide a multiple-point anatomical reference system for aligning the drill sleeve in a desired position by contacting three separate knee joint locations. The guide assembly preferably contacts the trochlear groove, the femoral intercondylar groove and the tibial eminence.

The tibial drill guide also includes a removable guide bar that is operable to be slidably removed from one of a pair of apertures extending through the guide arm for use in either the right or left knee. In this regard, the guide bar is slidably received within one of the apertures and offset at about seventy degrees (70°) relative to the guide arm. For example, for anterior cruciate replacement on the right knee, the guide arm is aligned with the guide assembly contacting the trochlear groove, the femoral intercondylar groove and the tibial eminence. The medial to lateral rotation of the tibial guide is then visually sited using the guide bar, such that the guide arm is rotated medially toward the left knee until the guide bar becomes substantially parallel with the longitudinal axis of the tibia or the coronal plane. It has been determined that this positioning of the tibial tunnel at a seventy degree (70°) angle relative to the coronal plane is the optimal positioning of the tibial tunnel to reduce stress on the graft. The removable guide bar provides a quick and efficient means for aligning the tibial tunnel in this manner.

The drill guide may also include a collar attached to the guide assembly for holding the drill sleeve in a moveable relation. In this arrangement, the drill guide also includes means for securing the drill sleeve within the collar. This may be provided as a pin threaded into the elongated positioning member, passing through the collar and abutting against the drill sleeve. In another arrangement, this may be provided as a pin biased against the drill sleeve and a thumb-actuated lever by opposing springs.

In the method of the present invention, there is provided a method for replacement of an anterior cruciate ligament. This method includes a method for using the tibial drill guide set forth herein. The steps of the method include inserting the drill guide into a medial portal of a knee joint and positioning the drill guide in simultaneous contact with the trochlear groove, the femoral intercondylar notch and the tibial eminence. In the next step of the method of the present invention, the drill guide is utilized to conduct a drilling procedure, thereby creating a tibial tunnel. This may include using the drill guide to create a guide hole, which in turn is used to create a tibial tunnel.

Accordingly, it is an object of the present invention to provide a drill guide for determining the site for and drilling a tunnel in a tibia for anterior cruciate ligament replacement. A related object of the present invention is to provide a method for using the tibial guide device.

A further object of the present invention is to provide an apparatus and method for anterior cruciate ligament replacement which maximizes isometric placement of an ACL graft tunnel through a tibia.

Another object of the present invention is to provide an apparatus and method for anterior cruciate ligament replacement which minimizes impingement of an ACL graft upon implantation.

A further object of the present invention is to provide an apparatus and method for anterior cruciate ligament replacement which allows proper reaction of the replacement ACL to the PCL.

An additional object of the present invention is to provide an apparatus and method for anterior cruciate ligament replacement which determines proper custom placement of the tibial tunnel through the use of multiple reference points upon the surrounding bone anatomy.

Yet a further object of the present invention is to provide an apparatus and method for anterior cruciate ligament replacement which provides optimum alignment of the tibial tunnel relative to the coronal plane at about seventy degrees (70°).

Another object of the present invention is to provide an apparatus and method for anterior cruciate ligament replacement that minimizes roofplasty in the femoral intercondylar notch.

A further object of the present invention is to provide an apparatus and method for anterior cruciate ligament replacement that is convenient and quick to use.

Another object of the present invention is to provide an apparatus and method for anterior cruciate ligament replacement which recognizes that different patients may have different anatomical structure which may cause the determination of the optimum position for an ACL tibial tunnel to vary among patients.

A further object of the present invention is to provide an apparatus and method for anterior cruciate ligament replacement that references three locations upon the knee joint for determining proper location for the tibial tunnel.

Additional objects, advantages and features of the present invention will become apparent from the following description and appended claims, taken in conjunction with the accompanying drawings.

BRIEF DESCRIPTION OF THE DRAWINGS

Various advantages of the present invention will become apparent from the following specification and appended claims by reference to the following drawings in which:

FIGS. 1 and 2 are schematic perspective views of the harvesting of the tendons for use as an ACL replacement in accordance with the present invention;

FIG. 3 illustrates harvested tendons prepared for use as an ACL graft in accordance with the present invention;

FIG. 9 illustrates placement and use of the transverse drill guide to place the transverse femoral locator guide pin;

FIGS. 10 and 11 illustrate placement and use of the anterior tibial drill guide to position and place the tibial guide pin;

FIGS. 12 and 13 depict use of a tensiometer in isometrically determining the positioning of the osseous tunnels;

FIGS. 17 and 18 illustrate use of the unique sizer member in accordance with the present invention to determine possible ACL graft impingement in the intercondyle notch;

FIGS. 19 and 20 illustrate use of the unique gouge instrument to mark the location of the roofplasty necessary to eliminate possible ACL graft impingement;

FIG. 25 is a side cross-sectional view of the drill guide set forth in FIGS. 23 and 24;

FIG. 26 is an end cross-sectional view of the drill guide set forth in FIG. 25;

DETAILED DESCRIPTION OF THE PREFERRED EMBODIMENT

Figure 4:
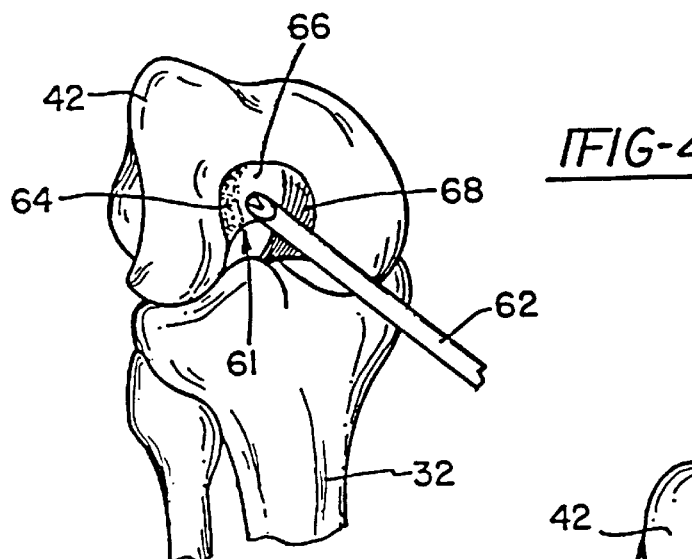
FIG. 4 is a schematic perspective view of the wallplasty procedural step for ACL reconstruction in accordance with the present invention.

It should be understood that while this invention is described in connection with particular examples, the scope of the invention need not be so limited. Rather, those skilled in the art will appreciate that the following teachings can be used in a much wider variety of applications than the examples specifically mentioned herein.

For a knee reconstruction involving an un-repairable or torn anterior cruciate ligament (ACL), the procedure begins with a general anesthesia being administered to the patient. The patient is positioned supine on the operating table. A well-padded tourniquet is placed proximal on the thigh of the affected leg, although the tourniquet is not inflated until later. An arthroscopic leg holder is placed around the tourniquet. The table is inclined (e.g. 15° of trendelenburg) and adjusted in height (e.g. waist level) according to the desires of the surgeon. The other leg is secured to the foot of the table. A Mayo stand is placed over the leg holder and positioned to permit access to the lateral thigh.

The surgical site is prepped and draped with a sterile seal. Standard arthroscopic draping is performed covering the Mayo stand. The light cord, camera, motorized instruments, and inflow, outflow and suction tubing are wrapped and secured to the drape on the Mayo stand. The irrigation stand is set up and positioned.

The joint of the affected leg is examined physically to confirm a rupture of the ACL and to determine the amount and degree of movement aoint looseness).

The graft harvesting step in the procedure depends on the type of ACL substitute that is to be utilized. In accordance with the present invention, preferably the gracilis and semitendinosus tendons are harvested from the patient and used as the ACL substitute. These provide a graft which is stronger in the joint (over twice the strength of the original ACL) and has less postoperative morbidity. However, it is also possible in accordance with the present invention to use other known ACL substitutes, such as patellar tendons, autogenous tendons, frozen and lyophilized tendon allografts, or some of the various known synthetic materials. Although the harvesting and preparation techniques may be different or eliminated altogether with other ACL substitutes, their installation and attachment to the femur and tibia are preferably the same as that described below relative to placement and attachment of harvested semitendinosus and gracilis tendons.

A tibial incision is used for harvesting the semitendinosus and gracilis tendons as well as for use as the site for making the tibial tunnel. The anterior tibial crest and the posteromedial margin of the tibia are outlined with a marking pen. The incision overlies a line which bisects that outline. A longitudinal incision about 4cm in length is centered at a point about three finger widths distal to the anteromedial joint line over the bisecting line.

The incision is made with a No. 15-blade through the skin and subcutaneous tissue. Electrocautery is used for hemostasis. Subcutaneous fat is elevated off the sartorius expansion from the anteromedial tibial crest to the posteromedial tibial edge. A rake is used to medially displace the medial edge of the incision and the gracilis tendon is palpated.

An incision 30 is made in the tibia 32 parallel and inferior to the gracilis tendon by cutting through the sartorius expansion (see FIG. 1). The incision is angled 90° proximally along the medial tibial crest of the tibia 32 for approximately 15 mm. With the knee at 90° the gracilis tendon 34 is isolated manually and a penrose drain or equivalent device is passed around it to maintain tension on it. The tendon is detached carefully from the tibia preserving maximal length.

As shown in FIG. 2, the detached end 36 of the tendon 34 is prepared for grasping by installation of sutures 38 using a No. 1 Ethibond suture and a tendon needle. A number of "whip" stitches are weaved about 4 cm up along each side of the detached tendon.

The tendon 34 is cut free from attachments along its length by metzenbaum scissors. The sutures 38 are tugged gently until the tendon can be seen to move freely.

The gracilis tendon 34 is removed by a tendon stripper 40, such as the closed end or slotted end tendon strippers marketed by Arthrotek of Warsaw, Indiana. After the loose end of the tendon is positioned in or threaded through the stripper instrument 40, the tendon is grasped and held in tension manually by the sutures 38. The stripper 40 is slowly advanced up the length of the tendon until the tendon is completely separated from the femur 42 and delivered. The stripper circumferentially divides the tendon using its sharp leading edge 44. With this procedure, the length of the harvested tendon is maximized. The length of the tendon should be sufficient so it can be "double looped" when used as the ACL replacement graft.

Precisely the same steps and procedures are used to isolate, detach and harvest the semitendinosus tendon. The length of the semitendinous tendon should also be maximized so it can be "double-looped" into a strong graft.

After the two grafts are harvested, they are prepared and sized. (The preparation and sizing steps can be performed by a surgical assistant while the surgeon continues with the rest of the ACL replacement procedure). Any remaining muscle fibers are removed from the grafts and whip stitches are made with No. 1 Ethibond sutures approximately 4 cm from the proximal end of each tendon. FIG. 3 shows a double looped gracilis tendon 34 and a double looped semitendinous tendon 46. The sutures 38 are attached to the free ends of the tendons with the whip stitches 48. For identification of the tendons and associated sutures, the sutures on each tendon can be tied with a different number of knots (e.g. two knots in the semitendinosus sutures and one knot in the gracilis sutures).

The pair of double looped tendons 34 and 46 are bundled together to form a composite graft 52. An umbilical tape 50 is looped around the midpoint of both tendons and is later used to pass the tendons through the osseous tunnels, as explained below.

In order to determine the proper size of the osseous tunnels, the bundled graft 52 (together with the umbilical tape and sutures) are passed through conventional incremental graft sizing tubes. An average graft should fit snugly into an 8 mm sizer which provides a 50 $mm^2$ cross-section identical in size to an average ACL. The proper diameter for reaming is obtained when the graft 52 firmly fits in the sizer; it should not be loose.

If another type of ACL graft is to be utilized instead of the gracilis/semitendinous tendon graft 52, it should be prepared in a similar manner. Sutures should be attached to the ends of the graft to aid in grasping, manipulating and securing the graft in place. Incremental sizing tubes are used to size the graft and select the appropriate drills for forming the tunnel. Installation and attachment of the graft to the femur and tibia are essentially the same as that which will be described below relative to placement and attachment of graft 52, although other conventional or standard procedures may be utilized.

The prepared knee is now examined by arthroscopic procedures. Standard anterolateral and anteromedial portals are made for the diagnostic arthroscopy. Proper portal placement is important. Preferably, the lateral portal is made at a location one-third the width of the patella ligament medial to the lateral margin and positioned vertically just inferior to the inferior patella tip. The medial portal is made vertically, just inferior to the inferior patella tip and adjacent to the medial border of the patella ligament. The two portals should be located at the same level.

The fat pad is pushed away from the area by distension of the knee and diagnostic arthroscopy is performed. Any observed meniscal damage, osteophyte and unstable joint surfaces are appropriately treated by standard arthroscopic techniques and the status of the cruciate ligaments is confirmed.

Debriding and sculpting of the lateral side of the intercondylar notch 61 is then performed (still without inflation of the tourniquet). This is commonly called wallplasty. Preferably a 5.5 mm full-radius synovial resector is used through the medial portal. A conservative trimming of the fat pad is accomplished, starting laterally and ending medially. These steps allow better observation of the notch.

The wallplasty is performed using a notchplasty gouge 62, as shown in FIG. 4, to remove 3–5 mm of the lateral condylar wall 64. No bone is removed from the intercondylar roof 66 at this point.

An up-angled, curved and uterine curette is used through the medial portal to remove the origin (and stump) of the ACL from the intercondylar roof and the wall of the lateral femoral condyle. The retained synovial and cruciate remnants are cleaned and vacuumed with a full-radius resector. (Care should be taken to protect the PCL 68 and avoid injury to it and its synovium). Preparation is complete when a probe can be used to palpate the posterior ridge of the intercondylar roof 66 with clear, unobstructed visualization.

The site for placement of the femoral guide pin is then selected. This is the first step in determining the location of the osseous tunnels in the femur and tibia. The placement of these tunnels is important since they must enter the joint at the proper anatomic attachment points (where the original ACL was attached).

Figure 5:
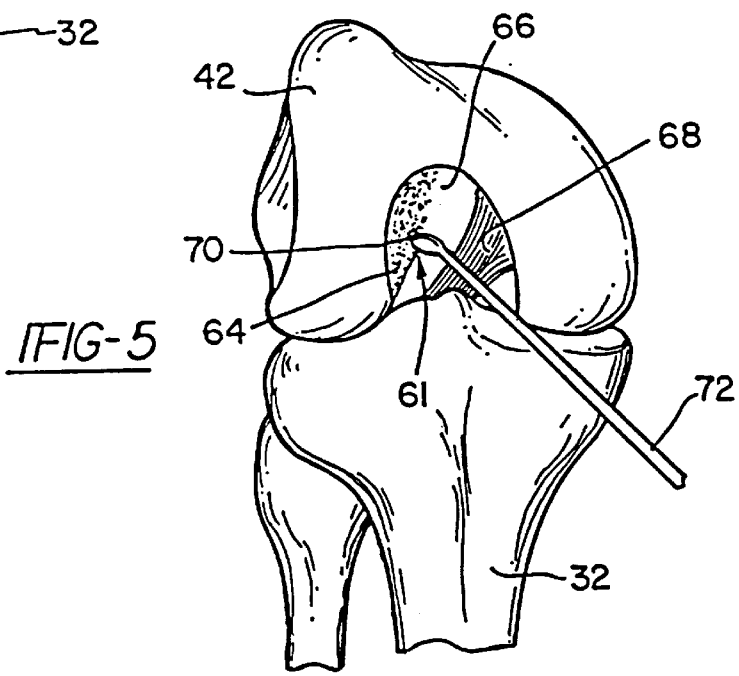
FIG. 5 illustrates the marking of the femoral attachment site with a curette.

The reference point for determining the location of the intra articular entrance point of the femoral guide pin is the posterior arch of the intercondylar notch. A nerve-hook probe is manipulated through the medial portal until the angled tip is oriented at the surgeon's discretion relative to the floor and camera projection (preferably perpendicular). The tip of the probe is positioned to cradle the posterior edge of the intercondylar notch in the over-the-roof position. The tip is then slid forward about 5 mm from the posterior edge and rotated either to the 11:00 position (for a right knee) or the 1:00 position (for a left knee). This position is then marked by boring a small recess 70 with an angled cervical curette 72. This is shown in FIG. 5. The pin site selection is confirmed by palpating with the probe.

The arthroscopic instruments and fluid are removed from the joint. The leg is exsanguinated and the tourniquet is now inflated. Next, the lateral femur is exposed.

Figure 6:
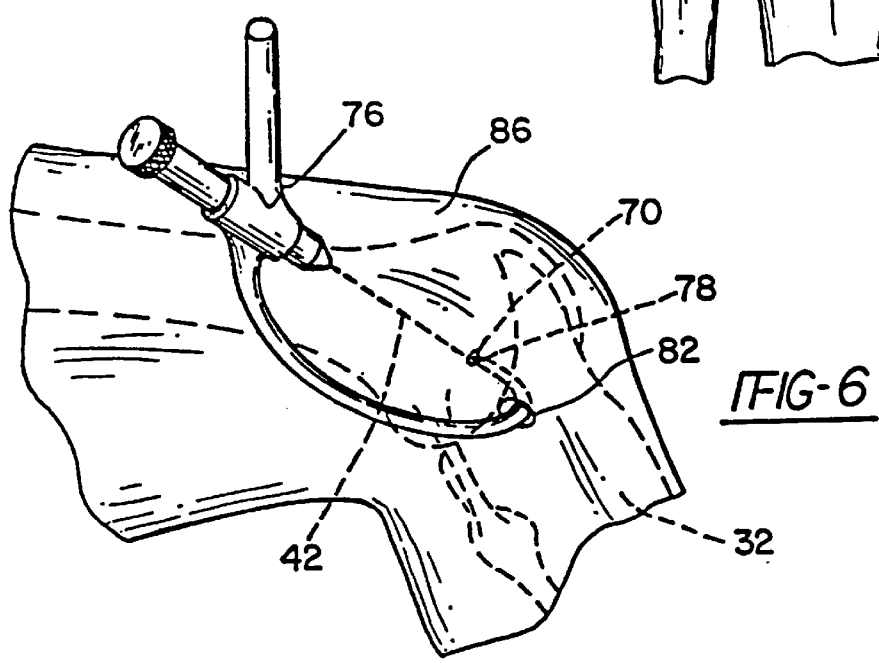
FIG. 6 illustrates the marking of the location of the lateral femoral incision.

The site for the incision on the lateral femur is then determined. This can be determined visually from experience or teaching, or a guide instrument can be utilized. The front entry guide system by Acufex Microsurgical, Inc. can be used, for example, as shown in FIG. 6. The guide 76 is brought into the joint through the lateral portal 82 and the tip 78 is centered in the small recess or hole 70 marked previously with the curette. The remaining portion of the guide 76 is brought to rest on the skin 86 overlying the anterolateral femur, just proximal to the metaphyseal flair.

An incision about 4 cm in length is made just proximal to the medial epicondyle and parallel to the long axis of the femur. If the incision site is too anterior the guide 76 will not rest on the lateral aspect of the skin. If it is too posterior, the guide will hang up on the anterior skin.

Figure 7:
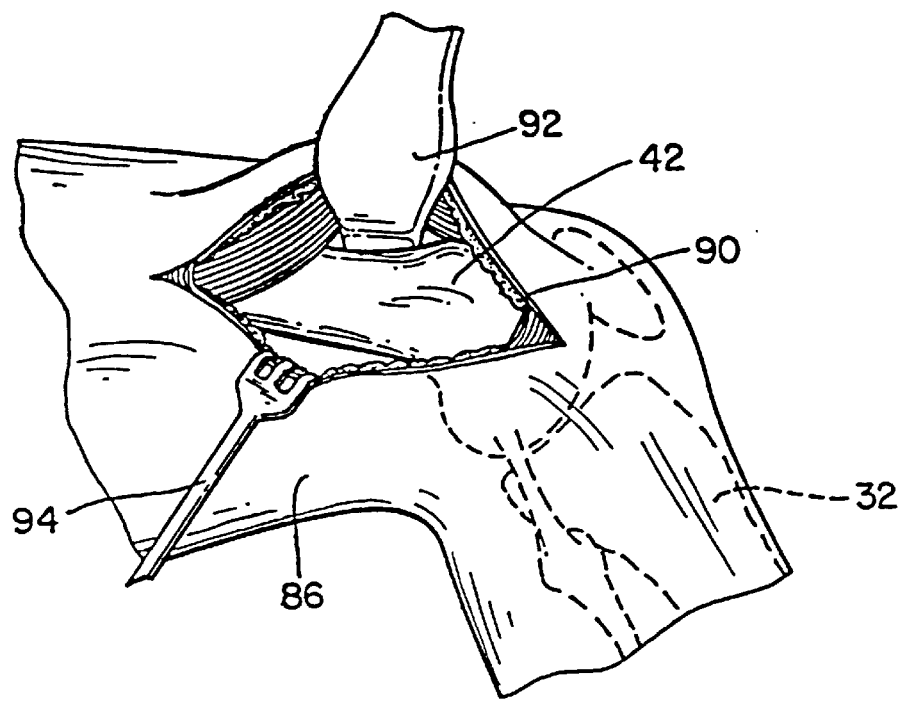
FIG. 7 illustrates the lateral femoral incision procedure.

A skin incision 90 is made through the IT-band and the subcutaneous fat is swept off posteriorly. This is shown in FIG. 7. The IT-band is incised and the incision extended distally approximately 10 cm up the thigh. A lateral retractor 92 is placed between the periosteum and muscle mass. The superior lateral geniculate vessels are identified and cauterized. The periosteum is incised longitudinally and the lateral retractor 94 is replaced deep to it on the anterior femur and stabilized.

Figure 8:
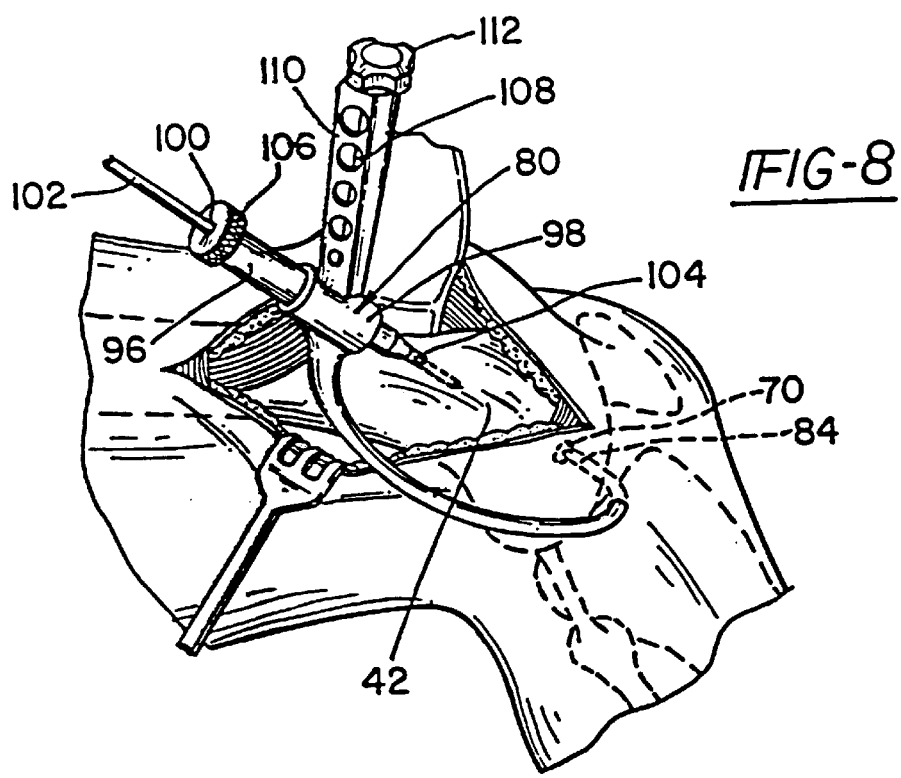
FIG. 8 shows drilling and positioning of the femoral guide pin with the rear entry guide.

As shown in FIG. 8, a rear entry drill guide 80, such as the Acufex Microsurgical rear entry drill guide system, is then used to drill the hole for the femoral guide pin. The drill guide 80 is positioned and placed in the joint by a gaff. The tip 84 of the guide is secured in the recess 70. A "bullet" (drill sleeve) 96 is placed in the drill sleeve collar 98 of the drill guide 80. The drill sleeve 96 is hollow having a passageway 100 for placement therethrough of a sharp pointed wire-type drill 102, such as a K-wire. The front end 104 of the bullet 96 has a sharp tni-point and the rear end 106 has a knob for ease of grasping and manipulation.

Once the tn-point bullet 96 is positioned in the tubular collar 98 with the tip against the appropriate position on the lateral cortex of the femur 42, it is locked in place by a long threaded rod 108 positioned in handle 110 of the, drill guide 80 and operated by turn knob 112. The rod 108 is threaded through a threaded opening (not shown) in the collar 98 and makes contact with the bullet 96. When the rod is rotated by the knob, it forces the bullet in a fixed engaging relationship with the inner wall of the collar 98 holding the two members firmly locked together.

Once the drill guide 80 and bullet 96 are firmly set in place, the wire drill (K-wire) 102 is passed through the bullet and drilled into and through the femur using a conventional surgical motorized drilling instrument. Due to the shape of the drill guide 80, the drill 102 placed in the bullet 96 will always hit the tip 84 of the guide wherever it is placed. Preferably a 2 mm wire drill is used.

After accurate positioning and placement is confirmed arthroscopically, the wire drill is drilled into and out of the passageway several times (preferably 8–10 times) to make a uniform tunnel. The bullet 96 is then released from the collar 98 and removed from the guide 80, leaving the K-wire (or substituted guide pin) in place. The drill guide 80 is also removed.

If desired, a 6 mm cannulated reamer is used to broach the outer femoral cortex to outline the pin tract so that the wire drill or guide pin can be removed. A 1-PDS suture, loaded on an 18-gauge spinal needle, is then passed into the joint through the drilled hole.

It is also possible in accordance with the present invention, to make the femoral tunnel in another manner. For example, the femoral tunnel could be made using Acufex's endoscopic system or front entry guide system. Other conventional procedures can also be utilized.

Figure 11:
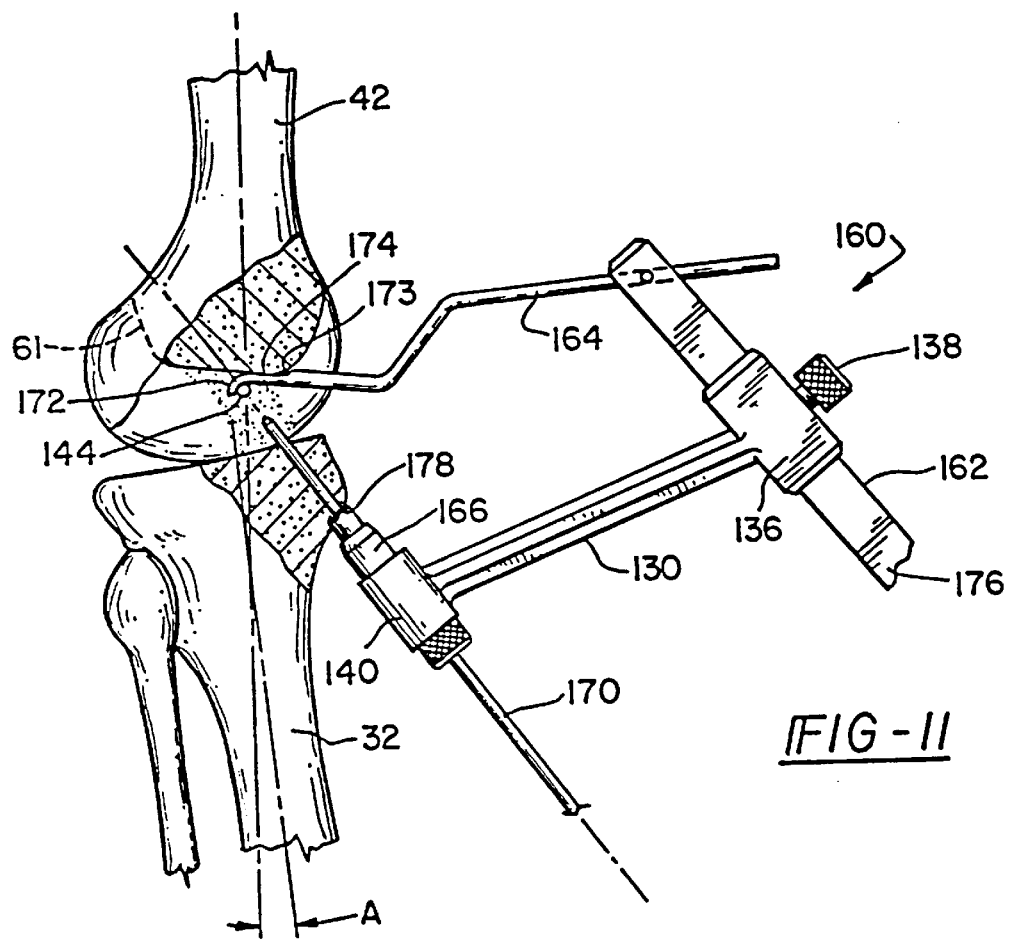

Once the positioning of the femoral guide pin has been established indicating the prospective position of the femoral tunnel for the ACL graft, the position for the guide pin for the proposed tibial tunnel is determined. A set of unique drill guides of the shape and structure shown in FIGS. 9–11 are used to position and place the Uibial guide pin.

First a transverse drill guide 120 is utilized (FIG. 9). The guide 120 has an elongated slide bar 122, a bent wire aimer 124 with a curved tip 126, a wire drill sleeve 128, and a drill sleeve positioning member 130. The aimer 124 has a notch 132 defining a convex flattened top surface, and is adapted to nest in and mate with the cartilaginous surface 134 of the intercondylar notch 61. The tip 126 is curved about 90°.

The positioning member 130 has a base 136 which has a channel in it to allow the member 130 to fit over and slide along the slide bar 122. A threaded set screw 138 with an enlarged head for manual grasping and tightening is used to hold the member 130 in the desired position on the slide bar. The drill sleeve 128 is received in a collar 140. The collar 140 has internal threads which mate with a series of external threads on the outer surface of the sleeve 128 so that the sleeve can be secured in place relative to the collar. The sleeve 128 has an enlarged end 142 which is used to manually turn and tighten the sleeve in the collar. The sleeve 128 has a central passageway 129 through it for holding and positioning a wire-type drill 144.

In use, the transverse tibial drill guide 120 (without the positioning member 130 thereon) is first put into position. The bent wire aimer 124 is brought through the anteromedial portal 150 and aligned so that the notch 132 is positioned against the cartilaginous surface 134 of the anterior edge of the intercondylar notch. (If the position of the portal 150 is not appropriate, then another portal, such as a central patellar portal, can be made and utilized). More particularly, the aimer is placed against the roof 66 of the intercondylar notch 61 with the knee at about 30–45° flexion. The notch or "step-off" 132 is placed against the anterior aspect of the notch. The guide 120 is held firmly in this position approximately perpendicular to the longitudinal axis of the tibia and femur.

The drill sleeve 128 is tightly threaded into the collar 140 of the positioning member 130 and the positioning member 130 in turn is placed on the slide bar 122. The member 130 is moved along the bar 122 toward the aimer 124 until the end 152 of the drill sleeve 128 abuts the lateral external surface of the thigh.

A wire drill 144, which preferably is a 0.062 diameter K-wire, is positioned in the drill sleeve 128 and drilled by any conventional motorized drilling mechanism through the lateral femur, (as shown in FIG. 9). The wire drill passes from lateral to medial in the femur 42 to outline a window to contain the tip of the anterior tibial drill guide 160 (as shown in FIGS. 10 and 11) between the intercondylar roof 66, the lateral edge of the PCL 68, and the medial wall of the lateral femoral condyle 64. The wire drill is advanced just to or into the PCL and not into the medial femur.

Once the wire drill 144 is installed in place in the femur 42, the transverse drill guide 120 is removed. The positioning member 130 is loosened and removed from the slide bar 122, and the aimer 124 is removed from the medial portal. Since the wire drill 144 (or substitute guide pin) is left in position in the femur, it is necessary to rotate the aimer in order to remove it from the joint. If there is difficulty in removing the hook of the transverse guide from the transverse pin, the pin can be backed away from the PCL until the hook is removed and then readvanced.

Once in place the wire drill (K-wire) 144 becomes a transverse locator pin (although it is also possible in accordance with the present invention to replace the wire-type drill with a guide pin). The drill or pin is positioned in the joint a few millimeters distal to the roof 66 and enters the medial side of the notch approximately where the PCL is attached.

The anterior tibial drill guide 160 is then put into position through the anteromedial portal. This is shown in FIGS. 10 and 11. This drill guide 160 has an elongated slide bar 162 and a bent wire hook 164. The positioning member 130 which is used on the transverse drill guide 120 to position and place the drill 144 acting as the transverse guide pin 144 is also used with the anterior tibial drill guide 160.

The base 136 of the positioning member 130 fits over and slides along the slide bar 162. The screw 138 is used to hold the member 130 in place on the bar once it is put in its proper position. A tri-point "bullet" drill sleeve 166 is positioned in the collar 140. A series of threads on the outer surface of the bullet 166 mate with the threads on the inner surface of the collar 140 and are used to tightly hold the bullet in position within the sleeve 140. The bullet 166 has a central passageway 168 through it for holding and positioning a wire drill (K-wire) 170.

With the knee slowly being extended, the hook 164 is brought into the joint through the anteromedial portal. The hook is rotated and the curved tip 172 of the hook 164 is positioned within the "window" over the drill 144 acting as the transverse guide pin. This sets the position for accurately drilling and setting of the tibial guide pin in the proper orientation and position. A curved notch 174 defining a convexly curved and flattened upper surface of the hook 164 is pushed posteriorly until it is positioned against the anterior aspect of the intercondylar notch 61 and the hook is tightly held in this position. For this procedure, the knee is deflated by removal of irrigation fluid and the knee is placed in maximum hyperextension, usually 5–10°, as shown in FIG. 11.

The anterior tibial drill guide 160 is raised or lifted until the flat upper surface 173 of the hook 164 is substantially perpendicular to the long axis of the femur 42. The concave lower surface of hook 164 is shaped to receive and nest with the drill 144 acting as the transverse pin. Resistance will be felt as the guide attempts to angulate the transverse pin.

The bullet drill sleeve 166 is positioned in the member 130 and tightly screwed into place. The member 130 is then slid over the end 176 of the slide bar 162 until the tri-point end 178 of the bullet abuts against the cortex of the tibia 32. With the hook 164 held tightly against the intercondylar roof and the drill guide 160 held perpendicular to the longitudinal axis of the femur, the bullet drill sleeve 166 is set in the proper position. The wire drill 170 is placed in the bullet 166 and drilled through the tibia into the joint by any conventional motorized drilling mechanism.

The wire drill (K-wire) 170 is drilled into and out of the drilled hole several times to create a uniform tunnel. The positioning member 130 and drill guide 160 are removed. It is also possible to remove the drill 144 acting as the transverse guide pin at this point since it has fulfilled its intended purpose, and substitute a guide pin for the wire drill 170 if desired (or remove it entirely).

The location of the original ACL fibers on the tibial joint surface are used as a landmark to check on 30 the placement of the tibial guide pin. The pin should protrude from the tibia into the joint at the original ACL site. When the knee is at maximum passive hyperextension, the pin should be parallel and 4–5 mm posterior to the intercondylar roof. If the drill 170 is too lateral or medial, then refinement of the guide pin alignment can be accomplished with a 3 or 5 mm hole changer.

The femoral drill hole formed in the manner described earlier and the tibial drill hole formed in the manner described immediately above should be in alignment and substantially parallel to each other. Once they are formed, their positions are checked to determine if they are properly placed isometrically.

In order to assess isometry of the two drill holes for use as the positioning for the osseous tunnels, a suture is first passed through them. This is shown in FIGS. 12 and 13. The suture 180 loaded on the spinal needle in the femoral drill hole 182 is grasped by a grabber in the joint and pulled through the tibial drill hole 184. A 2 mm suture passer also is utilized.

A sterile button 186 is tied on the femoral side of the suture and the stitch is pulled through the joint until the button lies flush on the femoral cortex. A tensiometer (or "isometer") 188 of conventional or known design is used to test the isometry of the drilled holes. The suture 180 is passed through the tensiometer 188 by a suture passer (not shown). The 2 mm tip 190 an the tensiometer is passed up the tibial drill hole 184 until the slanted surface 192 is firmly seated on the tibial cortex. (See FIG. 13.) The suture 180 is pulled tightly through the drill holes 182 and 184 and fastened securely to the end 194 of the tensiometer 188.

The tensiometer 188 is essentially a spring loaded strain gauge. One of the preferred types of tensiometers which can be used in accordance with the present invention is shown and described in the article entitled "ISOMETRIC PLACEMENT OF SUBSTITUTES FOR THE ANTERIOR CRUCIATE LIGAMENT", by Ben Graf, M.D.

Figure 14:
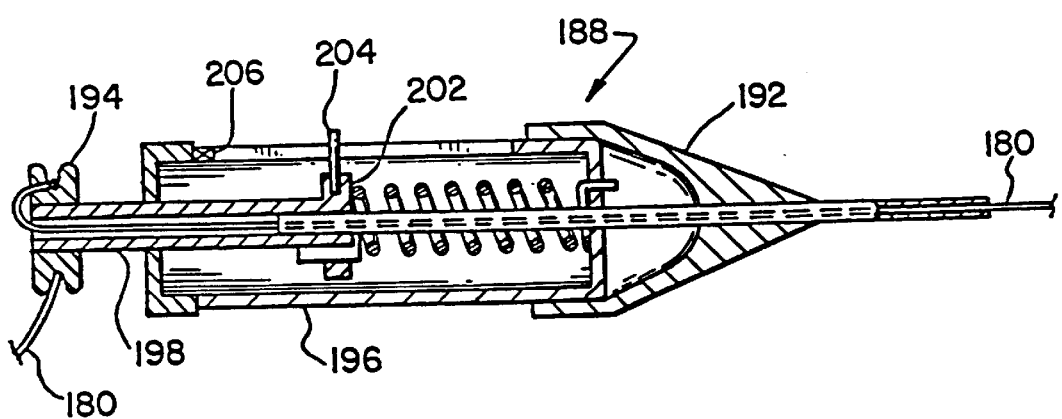
FIG. 14 is a cross-sectional view of the tensiometer shown in FIGS. 12 and 13.

As shown in FIG. 14 (together with FIGS. 12 and 13), the tensiometer 188 has a slanted front surface 192, a housing 196, a plunger member 198 and a coil spring 200. The plunger 198 fits within the housing 196 in a sliding telescopic relationship. The internal end 202 of the plunger is connected to the coil spring 200 which in turn is connected to the inside of the housing. The end 202 also has a locking post 204 which is adapted to slide along slot 206 or be locked in position in a bayonet or "J-shaped" slot 208. The spring 200 biases the member 198 relative to the housing.

A scale 210 in millimeters is arranged along the edge of the slot 206 so readings can be made of the relative position of the post 204. Preferably, the center of the scale at the entrance to the J-shaped slot 208 is set at "zero" so that positive and negative strain gauge readings from the zero point can be read in millimeters depending on the movement of the post during operation of the tensiometer 188.

Once the suture 180 is tightly held in position by the button 186 and tensiometer 188, the tensiometer is unlocked (i.e. the post 204 is moved from the J-shaped slot 208 to the main slot 206). The knee is manually taken through the range of motion from 0–110° and the excursion of the post 204 on the tensiometer is noted.

If the post movement is less than 1.5 mm then the correct femoral and tibial tunnel sites have been determined. If the readings are not within this range, then additional drill holes are made in the manner as described above and the isometric test is repeated.

Once isometry is obtained, the tensiometer 188 and suture 180, together with the button 186, are removed and the guide pins are replaced in the femoral and tibial drill holes. (This replacement should be checked, especially in patients with soft bones, to be certain that the pins have followed the correct pathways into the joint.)

Figure 15:
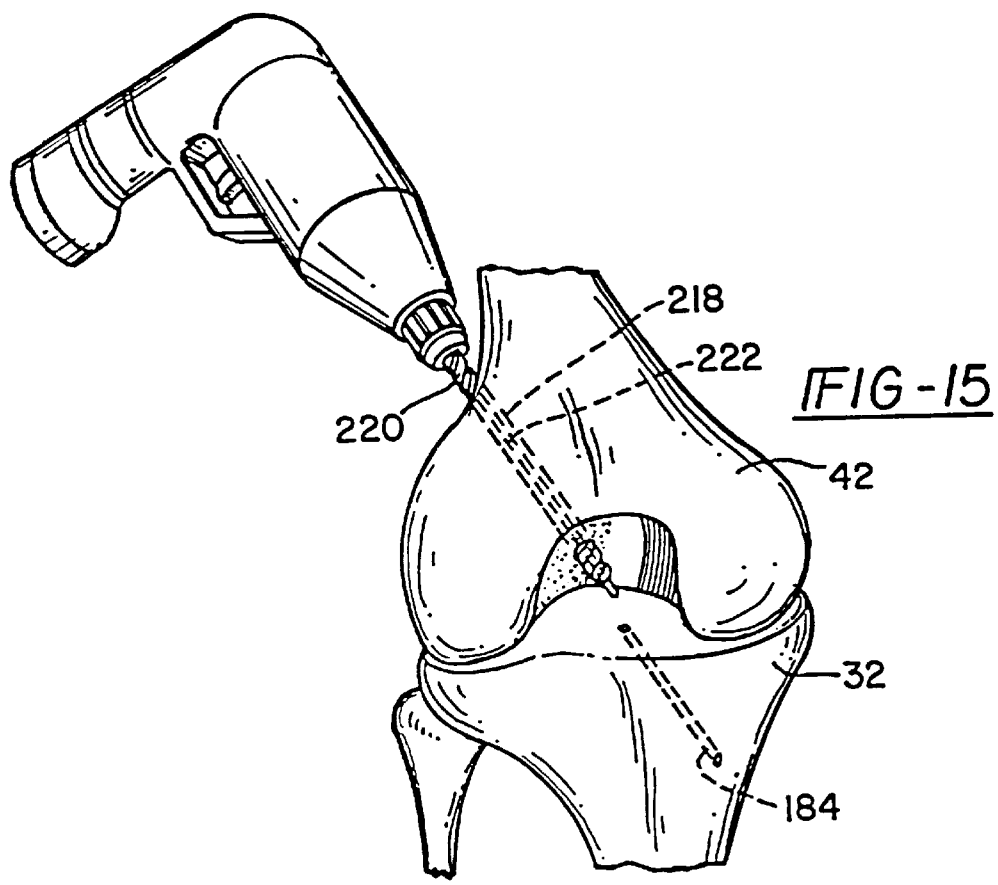
FIG. 15 illustrates the drilling and formation of the femoral tunnel.

The femoral tunnel 218 is then drilled using a properly sized cannulated reamer 220 over the guide pin 222. See FIG. 15. As mentioned earlier, the size of the tunnel is determined based on the snug fit of the double looped tendon graft 52 in a graft sizer. The reamer 220 should be controlled and viewed arthroscopically when it enters the joint to prevent inadvertent damage to the intercondylar contents. Preferably, the reamer is drilled in and out of its passageway 8–10 times in order to make a uniform tunnel. All bone fragments are irrigated from the joint.

Once the tunnel 218 has been formed, the edges or intra articular margins of the tunnel in the joint are smoothed and chamfered with a curved rasp. The rasping should be conservative to avoid changing of the position of the tunnel. The smoothing of the tunnel entrance into the joint prevents abrasion and potential damage to the graft. A properly sized tunnel plug (not shown) is inserted in the femoral tunnel temporarily and the joint is fully distended.

Figure 16:
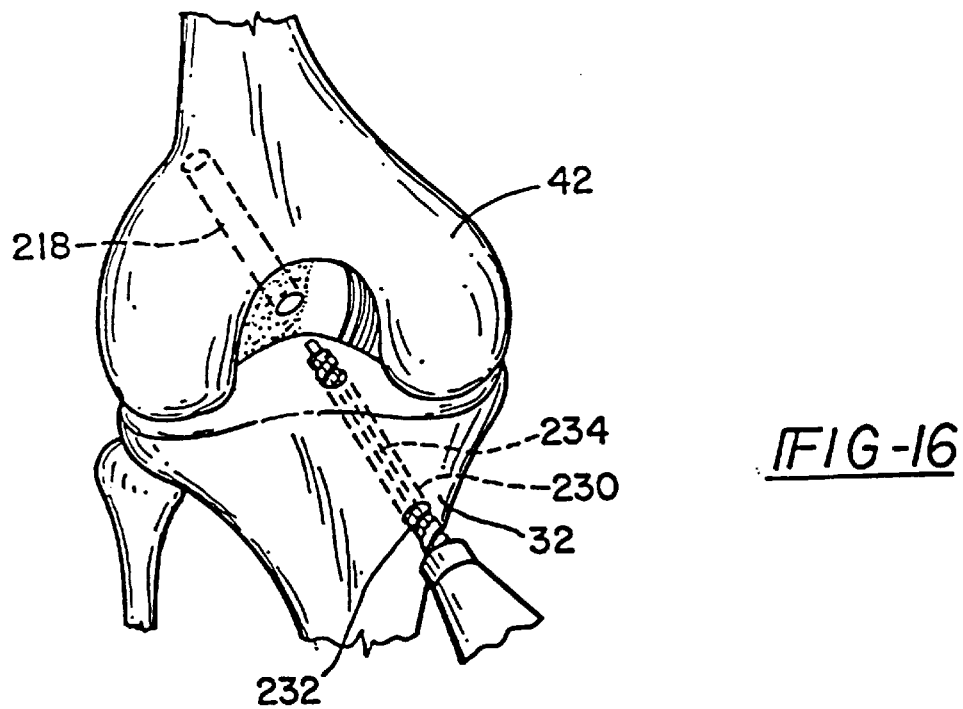
FIG. 16 illustrates the drilling and formation of the tibial tunnel.

The same procedure is used to drill the tibial tunnel 230. This is shown in FIG. 16. A properly sized cannulated reamer 232 is used to drill the tunnel over the guide pin 234. All bone chips and fragments are removed in a conventional manner and the tunnel edges are smoothed and chamfered with a rasp. A temporary hole plug is usually not needed on the tibial side because the ACL remnant at its insertion site seals the hole. A plug can be used if needed or desired, however.

After the two osseous tunnels 218 and 230 are finished, the possible impingement of the intercondylar roof on the substitute ACL graft is checked. This is accomplished by use of a unique calibrated sizer instrument 250 which has an elongated rod 252 and a handle member 254. (See FIGS. 17 and 18).

The handle member 254 preferably is knurled for ease of grasping and manipulation. In accordance with the invention, it is also possible to provide T-shaped handles or other types of handle members for the sizer instrument.

The rod 252 is graduated with a series of calibrated markings 256 thereon. The markings are in 5 mm increments and are used to determine the placement and positioning of the sizer relative to the tibial tunnel 230.

A sizer member is selected that matches the diameter of the newly drilled tibial tunnel 230. As shown in FIG. 17, the sizer member 250 is inserted in the tunnel so that the end 258 is positioned flush with the end of the tibia. The sizer is first inserted with the knee flexed at about 90°. The depth of the sizer 250 into the tibial tunnel is measured by noting the calibrated markings 256 on the rod 252. The knee, deflated of irrigation fluid, is then brought into maximum hyperextension. This is shown in FIG. 18. The amount of knee extension (angle "A") is measured by observing the angle between the femur and tibia from the side.

An attempt is made to push the sizer 250 into the joint. If the sizer cannot be pushed 25–35 mm into the joint, then notch impingement exists. The calibrated markings 256 are used to determine whether impingement is present.

The effect of untreated notch impingement on ultimate knee extension can be estimated by slowly flexing the knee while trying to advance the sizer into the notch through the tibial tunnel. The flexion angle at which the sizer can be advanced freely into the notch is observed. The difference in knee extension from that point to the point of maximum hyperextension indicates the amount of knee extension that would be lost if the impingement was not corrected.

If the sizer member passes all the way into the back of the notch (e.g. 30 mm mark) with the knee in hyperextension, then there is no impingement and it is unnecessary to cut the roof of the intercondyle notch.

Figure 20:
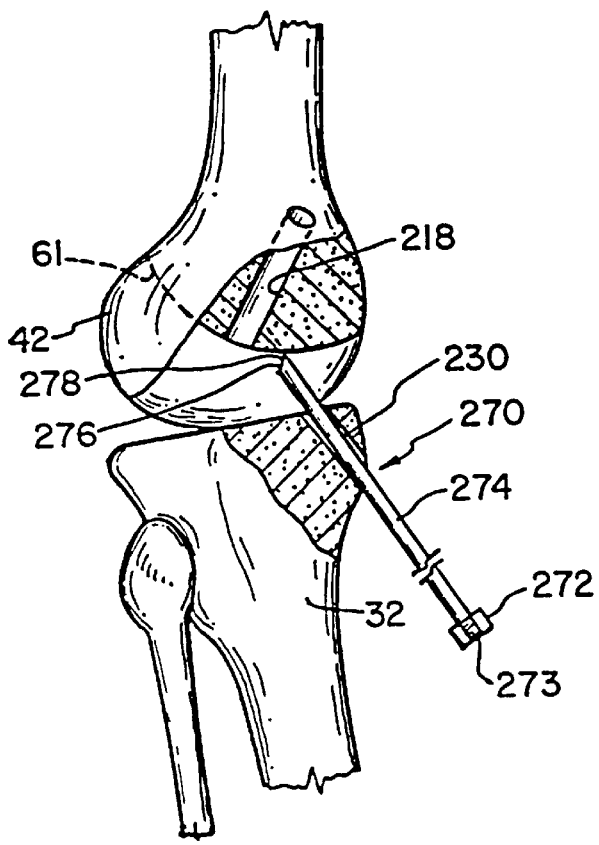

As is usually the case, impingement is determined to exist and a tailored roofplasty must be performed. Bone is removed from along the sagittal depth of the intercondylar roof. Preferably a gouge instrument 270 as shown in FIGS. 19 and 20 is used to mark the location of the required notchplasty on the roof 66 of the intercondylar notch 61 (i.e. "roofplasty"). The gouge has a handle member 272 at one end for ease of grasping and manipulation and an elongated shaft or rod 274. The end 276 of the shaft is angled and has a sharp pointed tip or cutting edge 278 on one side.

In accordance with the invention, the gouge 270 can have any type of handle member 272, such as a T-shaped handle or the like. Also, one side or edge of the handle member is notched or flattened 273 corresponding to the position of the cutting edge on the rod so that the surgeon will be better able to move and manipulate the tip in the joint.

The diameter of the shaft or rod 274 of the gouge instrument 270 is identically sized to match the diameter of the tibial tunnel 230. This allows for accurate marking of the roof impingement. With the knee maintained in hyperextension, the gouge 270 is passed through the tibial tunnel until the tip 278 abuts the intercondylar notch surface, as shown in FIG. 20. The location of the impingement is marked by striking the gouge with a mallet. The tip (or cutting edge) of the gouge is rotated as the gouge is struck forming an outline of the area of impinging bone which has to be removed. This outline is typically made in the arch formed by the intercondylar roof and lateral wall.

A tailored roofplasty is then performed, removing the outlined bone using one or more conventional hand-held gouges (not shown). Final smoothing and contouring of the roof is accomplished in a conventional manner using standard motorized burrs and hand-held rasps.

After the roofplasty is completed, the knee is again hyperextended and the sizer instrument 250 reinserted into the joint. If the impingement has been successfully eliminated, the sizer will pass unobstructed into and out of the joint and into the femoral tunnel 218. If there are still any obstructions, then additional roofplasty is performed and the sizer instrument inserted and the joint tested again until all of the possible impingement is removed.

In this manner, the possible impingement of the intercondyle roof on the substitute ACL graft is 20 identified, outlined, and quickly and accurately eliminated. Also, the amount of requisite bone removal is confirmed.

All of the possible impingement is removed before the graft is inserted in place which prevents any possible harm or damage to the graft if any impingements are not found until later and further notchplasty has to be performed with the substitute graft in place. Also, the present invention eliminates the need to perform extensive unnecessary protective notchplasty that is sometimes performed by "feel" in an attempt to insure against impingement.

Figure 21:
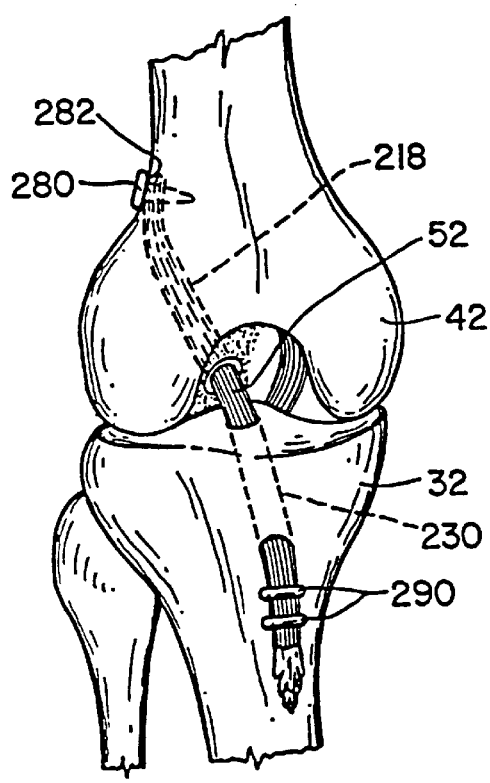
FIGS. 21 and 22 depict the positioning and securing of a tendon graft in accordance with the present invention.
Figure 22:
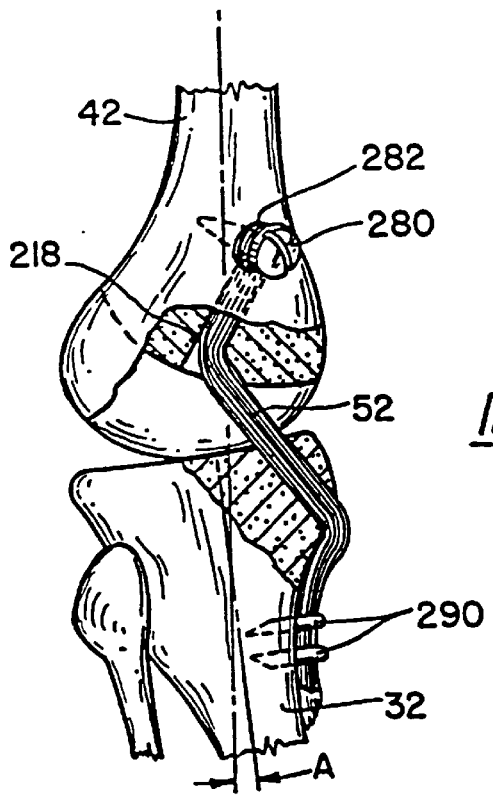

The next step is the placement and securing of the graft in the osseous tunnels. This is shown in FIGS. 21 and 22. The graft 52 (FIG. 3) is inserted in the tunnels and joint and permanently affixed in place. The graft 52 is passed through the tunnels starting with the tibial tunnel 230. An umbilical tape (not shown) is used to draw the graft 52 through the tunnels. The umbilical tape is first fed through the femoral tunnel 218 and positioned by forceps over the tibial tunnel. A grabber passed up the tibial tunnel 230 pulls the tape through the tibial tunnel where it is attached to the umbilical tape 50 previously looped around the tendons 34 and 46 or to the tendons themselves.

The double-looped graft 52 is then threaded through the tunnels 218 and 230 and pulled through the joint until the end passes out the lateral femoral cortex. About 2 cm of the double-looped tendon is passed 20 all of the way through the femoral tunnel and the end is held in place by a cancellous screw 280.

A 3.2 mm drill hole is made transverse across the femoral metaphysical flair, from lateral to medial at the junction of the linear aspera and the previously cauterized geniculates. The depth of the hole is measured and the hole is tapped for a 6.5 mm cancellous screw 280. The knee is brought into extension and maximally externally rotated. The cancellous screw 280 is placed in the hole with a ceramic ligament washer 282 being provided under the head of the screw. The end of the double-looped graft 52 is looped os10 around the screw and the screw tightened into the lateral cortex.

The sutures 38 which are attached to the other end of the graft 52 and protrude from the tibial tunnel are pulled tightly to remove any redundancies in the composite, tendon graft which can occur in snug, well-fitting tunnels. The sutures and graft are held firmly in tension by the surgeon and the junction of the tibial tunnel and graft 52 is palpated. The knee also is taken through a range of motion to check for "pistoning" (i.e. any excursion or movement of the graft in the tunnel). If there is no pistoning between 90° flexion and hyperextension, then the suitability and placement of the ACL graft is assured. For proper graft placement, the graft should slide less than 1 mm out of the tibial tunnel as the knee is brought from 0 to 120° of flexion. This "excursion profile" indicates that the graft will not stretch if it is secured to the tibia with the knee in full extension and external rotation.

The graft 52 is then affixed to the tibia 32 on the external surface of the tibia outside the tibial tunnel 230. Preferably, the end of the graft 52 is stapled in place with one or more serrated low profile bone staples 290. If desired, a small trench or channel (not shown) can be made in the tibia for placement of the end of the tibia. It is also possible in accordance with the present invention to secure the graft 52 or the sutures to a screw in the tibia similar to the manner in which the graft 52 is secured at its other end to the femur. Also, the ends of the graft containing the whip stitches can be trimmed from the graft after it is secured firmly in place.

When the tendons 34 and 46 have been properly harvested for the graft 52, sufficient length of tendon should remain extending out of the o10 tibial tunnel to allow placement of two staples 290. When insufficient graft protrudes, the graft can be secured with one staple and the sutures 38 can be tied to another staple.

After the graft is secured, the knee joint is tested with the Lachman and drawer tests. The knee should be tighter than the uninjured knee.

The graft is also finally examined arthroscopically to check for any impingements. If any are found, they are corrected and removed. After the graft is fully secured and examined in place, the wounds around the knee are closed and dressed, the tourniquet removed, a leg brace is installed, and appropriate postoperative care is followed.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

Figure 23:
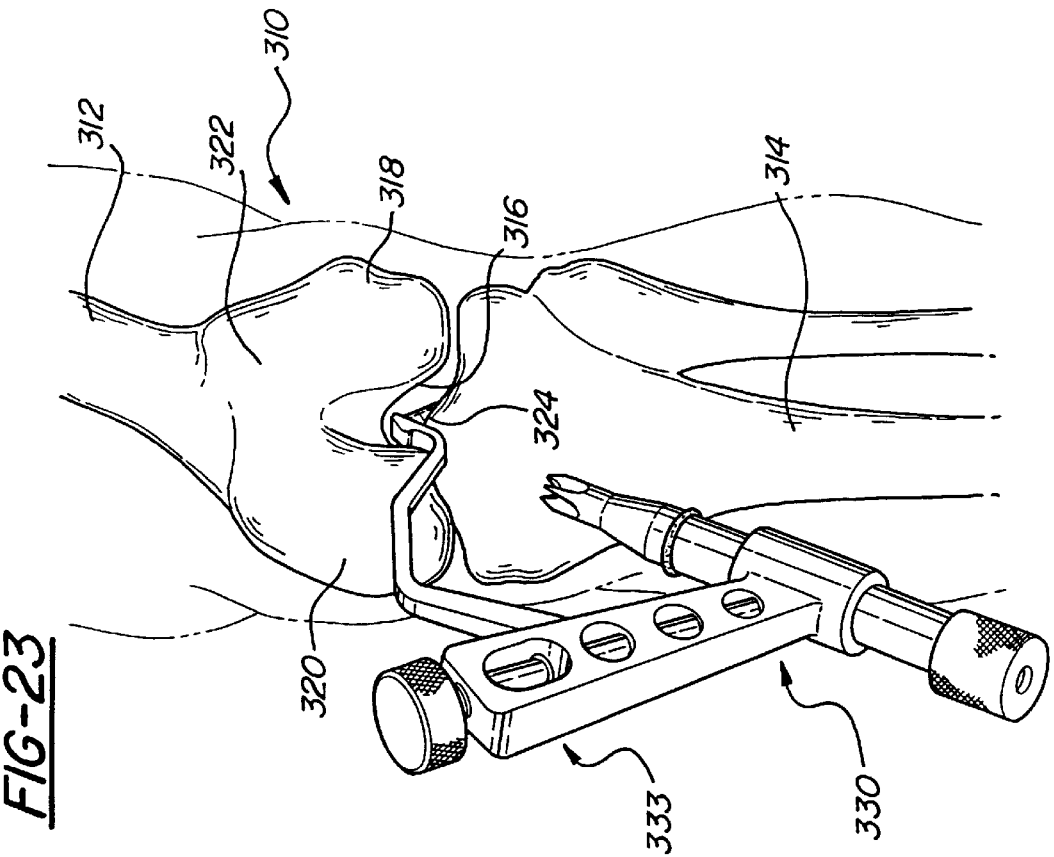
FIG. 23 is a perspective view of a drill guide according to the present invention prior to positioning for determining the proper site for a tibial tunnel.

Referring now to FIG. 23, there is shown a tibial drill guide device according to another embodiment of the present invention in operative association with a knee joint, shown generally at 310. The knee joint 310 includes a femur 312 and a tibia 314. The femur 312 is shown to include at its distal end a femoral intercondylar notch 316 formed between medial and lateral condyles, 318 and 320 respectively. The femur 312 is also shown to include a trochlear groove 322 located on the articular cartilage of the distal femur 312 where the patella articulates. The tibia 314 is shown to include a tibial eminence 324 which is typically a rounded protuberance disposed near the central surface at its proximal end. FIG. 23 also shows a tibial drill guide, generally designated by the numeral 330, in an inserted position within the knee joint 310 prior to its alignment for drilling a tibial tunnel.

The components of the tibial drill guide 330 will now be described with reference to FIGS. 24, 25 and 26. The tibial drill guide 330 includes a drill sleeve 332 for guiding a drilling procedure. Preferably, the drill sleeve 332 may be of an elongated cylindrical shape, although it will be appreciated that any suitable shape may be used. The drill sleeve 332 includes an aperture 334 for allowing the passage of a suitable drilling device, such as a K-wire or drill bit. Preferably, the aperture 334 has an axis 336 disposed along a longitudinal axis which may be its central longitudinal axis. To provide means for engaging the external surface of the tibia 314, the drill sleeve 332 also includes a tri-point tip 338 at its forwardmost end.

The drill guide 330 also includes a guide assembly 333 that provides a multiple-point anatomical reference system for aligning the drill sleeve 332 in a desired position. The guide assembly 333 accomplishes this multiple-point anatomical reference system by being able to contact several different reference points within the knee joint. Preferably, the guide assembly 333 is able to simultaneously contact the trochlear groove 322, the femoral intercondylar roof disposed at the top of the femoral intercondylar notch 316 and the tibial eminence 324. It will be appreciated, however, that this multiple-point reference system may contact other knee joint locations or may use other suitable reference points for aligning the drill sleeve 332.

In a preferred arrangement, the guide assembly 333 includes a positioning member 340 which may be in the form of an tapered elongated bar. The positioning member 340 may be of any convenient shape for ease in handling. The positioning member 340 may also include any surface irregularities or contours that facilitate gripping by hand. Some examples of these irregularities or contours will be described below in connection with FIGS. 27 and 28.

The drill guide 330 may preferably be in a configuration where the drill sleeve 332 is adjustable with respect to the guide assembly 333. In a preferred arrangement, the adjustability may be provided by disposing the drill sleeve 332 within a collar 342 attached to the positioning member 340 at its lower end. The collar 342 is shown to have an aperture 344 that corresponds to the configuration of the drill sleeve 332. Preferably, the aperture 344 is of a substantially cylindrical configuration and is sized to allow snug sliding movement of the drill sleeve 332 in a longitudinal direction within the collar 342. The axis of the aperture 344 is centrally located in the collar 342 and substantially corresponds to the axis 336 of the drill sleeve 332. It will be appreciated, however, that the shapes of the components set forth herein may vary and may be of any suitable shape. Further, it will be appreciated that the principle of relating one or more dimensional aspects of the drill sleeve 332 to the guide assembly 333, and in particular to the collar 342, may be accomplished while altering the shapes and dimensions of the components set forth herein.

To provide means for limiting the longitudinal travel of the drill sleeve 332 within the collar 342, the drill guide 330 further includes two limiting devices. In this regard, the drill sleeve 332 includes a knob 346 located at its rearwardmost end. The knob 346 is sized to a diameter larger than that of the aperture 334. This provides an abutment surface that limits forward travel of the drill sleeve 332 within the aperture 334 when the knob 346 abuts the rear edge of the collar 342. The knob 346 may preferably have a roughened external surface for facilitating manipulation of the drill sleeve 32 by hand. The drill sleeve 332 also includes an o-ring 348 for limiting rearward travel of the drill sleeve 332 within the collar 342. The o-ring 348 is preferably sized slightly larger than the diameter of the drill sleeve 332. In this configuration, the o-ring 348 provides enough resistance to prevent rearward travel of the drill sleeve 332 once it abuts against the forward edge of the collar 342. The o-ring 348 is preferably constructed of a compressible material such as an elastomeric rubber. Thus, the o-ring 346 may be deformed sufficiently to allow the drill sleeve 332 to be pulled through the aperture 344 in a rearward direction along with the remainder of the drill sleeve 332. This allows the drill sleeve 332 to be separated from the remainder of the drill guide 330.

To provide means for securing the drill sleeve 332 in a substantially stationary position within the collar 342, the drill guide 330 further includes a transverse pin 350 which is located within an aperture 352 of the positioning member 340. The transverse pin 350 abuts against the drill sleeve 332 with force sufficient to prevent the drill sleeve 332 from sliding within the collar 342. To provide means for maintaining force of the transverse pin 350 against the drill sleeve 332, the drill guide 330 further includes a thumb screw 354. The thumb screw 354 is located at the upper end of the transverse pin 350. The thumb screw 354 is threaded into a corresponding threaded bore 356 disposed at the top of the positioning member 332 until the distal tip of the transverse pin 350 abuts the drill sleeve 332 with sufficient force to hold the drill sleeve 332 in a stationary position within the collar 342.

To provide means for aligning the drill sleeve 332 in a desired position for formation of a tibial tunnel, the guide assembly 333 further includes a guide arm 360. In the arrangement shown in FIGS. 24, 25 and 26, the guide arm 360 is attached to the positioning member 340 near its uppermost end. It will be appreciated, however, that the guide arm 360 may be connected to the positioning member 340 at other locations. The guide arm 360 preferably includes a guide region, generally designated by the numeral 362, which is located at the forwardmost region of the guide arm 360. As will be more fully discussed below, the guide region 362 is configured to provide the multiple-point reference system for aligning the drill guide 330.

The guide region 362 of the guide arm 360 has several specialized sections that work simultaneously to accomplish the guiding procedure. These include a first guide section 364 formed as a first forward extension of the guide arm 360. The first guide section 364 is operable to contact the trochlear groove 322 of a knee joint. A second guide section 366 is formed as another portion of the guide arm 360 forward of the first guide section 364. The second guide section 366 is operable to contact the roof of the femoral intercondylar notch 316. The guide region 362 further includes a third guide section, provided as an extension 368, connected to the second guide section 366 at its forwardmost end. The extension 368 is an elongated protuberance shaped as a cylindrical section with a cone-shaped tip that includes a longitudinal axis 370. The extension 368 may be integrally formed with the second guide section 366 of the guide arm 360, or may alternatively be a separate element affixed to the second guide section 366. The first guide section 364, the second guide section 366 and the extension 368 are sized and oriented in specific relative sizes and configurations which will be described in greater detail below. The extension 368 includes three surfaces which aid in proper positioning and function of the drill guide 330. These include a tip 372 located at its distal end, a heel 374 located at the proximal end of the extension 368 and a stop 376 which is a flattened region located on the surface of the extension 368 facing the drill sleeve 332 in the region of the axis 336. It will be appreciated that the extension 368 may be integrally formed with the second guide section 366 of the guide arm 360 (as discussed below in connection with FIG. 27). The extension 368 may also be a separate element affixed to the second guide section 366, as shown in FIG. 25. Thus, the heel 374 may be either the end portion of the guide arm 360 or the upper portion of the extension 368. However, for purposes of simplicity and explanation, this component will be referred to as a portion of the extension 368.

Figure 24:
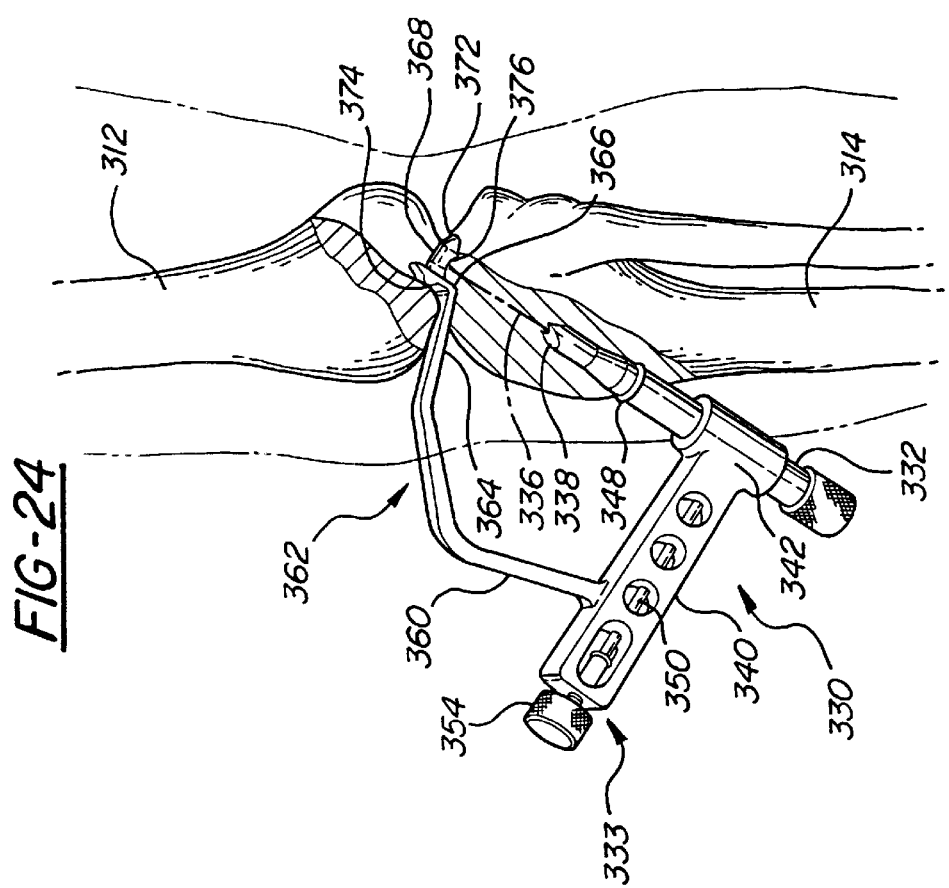
FIG. 24 is a partial cutaway view of a drill guide according to the present invention in position for determining the proper site for a tibial tunnel.

As shown FIG. 24, the tibial drill guide 330 performs its guiding frunction through the contacting of three surfaces of a knee joint. When placed in a fully inserted position with the knee in full extension or in slight hyperextension as shown in FIG. 24, the tibial drill guide 330 preferably guides the drilling procedure by being simultaneously locked in contact with three separate points of the anatomy of the knee joint 310 (e.g., the trochlear groove 322, the roof of the femoral intercondylar notch 16 and the tibial eminence 324). In this regard, the first guide section 364 contacts the trochlear groove 322, while the tip 372 of the extension 368 contacts the tibial eminence 324. At the same time, the heel 374 of the extension 368 contacts the roof of the femoral intercondylar notch 316.

It has been found that constructing the drill guide 330 to include several parameters enhances the ability of the drill guide 330 to properly locate the tibial tunnel. A first parameter is the angle $\Theta$ between the axis 336 and the longitudinal axis 370 of the extension 368. Preferably the angle $\Theta$ is approximately 100°±5°. A second parameter is the angle $\Phi$ between the first guide section 364 of the guide arm 360 and the axis 336. This angle is preferably approximately 70°±5°. Another parameter is the length of the extension 368, as measured in a direction perpendicular to the axis 336. This parameter, represented by the letter a, is preferably 20 mm±5 mm. Another parameter is the distance b, measured form the uppermost point of the heel 372 to the axis 336. This distance is preferably 5 mm±3 mm.

It will be appreciated that since the most favorable position for a tibial tunnel will depend upon the relative sizes and configurations of the femur and tibia, any or all the measurements set forth herein may be varied as necessary to determine the proper tibial tunnel location. For example, the dimensions of several or all of the components may be smaller or larger for use with smaller or larger patients. Thus, the proper size of drill guide 330 for a particular patient may be determined by reference to x-ray measurements of the patient's knee joint. Preferably, the drill guide 330 is constructed of 17-4 stainless steel, although it will be appreciated that any suitable material may be used.

Figure 28:
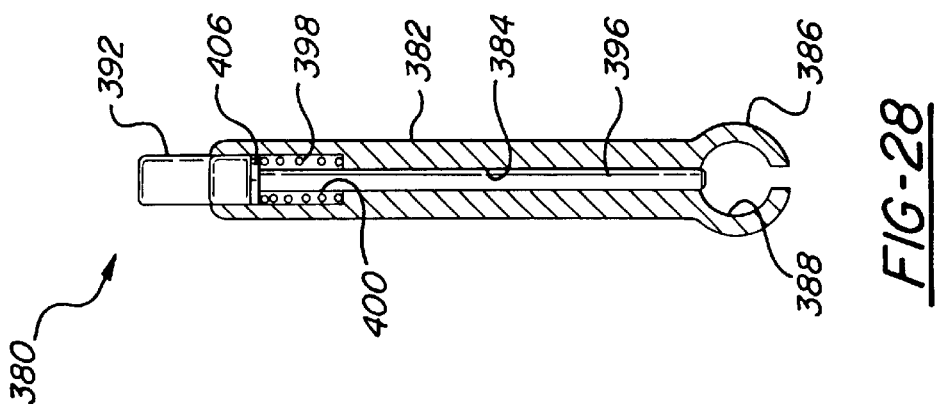
FIG. 28 is a end cross-sectional view of the drill guide set forth in FIG. 27.
Figure 27:
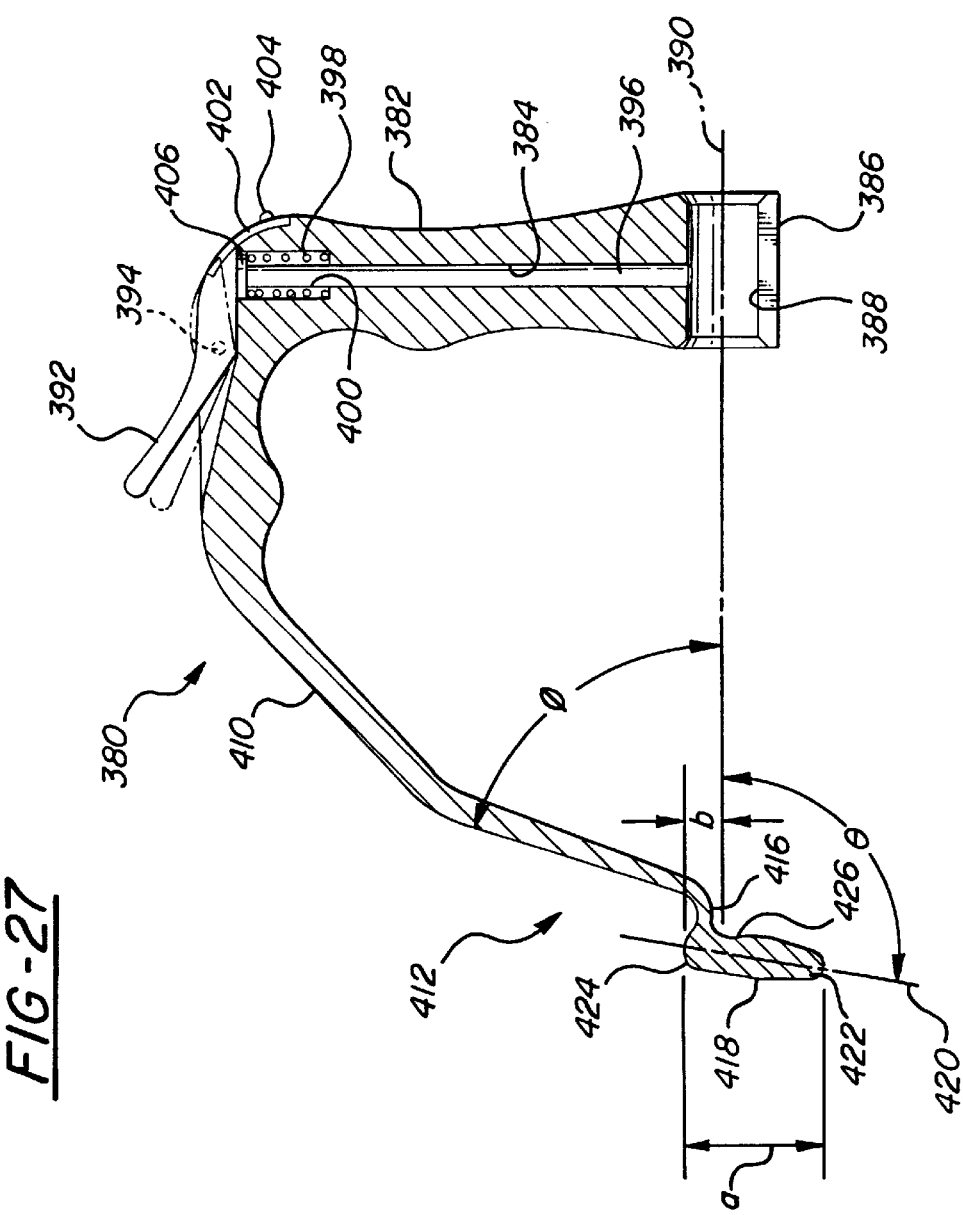
FIG. 27 is a side cross-sectional view of another version of drill guide according to the present invention.

Referring now to FIGS. 27 and 28, there is shown an alternate embodiment of the drill guide of the present invention which is generally designated by the numeral 380. The drill guide 380 includes a positioning member 382 that is contoured on its external surfaces for providing a hand grip. The positioning member 382 has an aperture 384 disposed upon a longitudinal axis thereon. A collar 386 is attached to the positioning member 382 at its lower end in substantially similar configuration to the previous embodiment of the drill guide 380. The collar 386 includes a cylindrically shaped aperture 388 whose central longitudinal axis defines a drilling axis 390. The aperture 388 is operable to allow the passage therethrough of a drill sleeve such as that shown at 332 in connection with FIGS. 24, 25 and 26. It will be appreciated, however, that the collar 386 may be a discontinuous piece of material as shown in FIG. 28.

To provide means for securing a drill sleeve 332 in a substantially stationary position within the collar 386, the drill guide 380 includes a lever 392 which is located near the top of the positioning member 382. The lever 392 pivots upon a pivot point 394 that is connected to the top of the positioning member 382. The lever 392 interacts with a transverse pin 396 disposed within the aperture 384 of the positioning member 382.

To provide an upward force for releasing the transverse pin from contact against a drill sleeve 332 disposed within the collar 386, biasing means is provided in the form of a coil spring 398. The coil spring 398 is preferably disposed within a recess 400 at the top portion of the aperture 384. To provide a downward force for causing the transverse pin to contact a drill sleeve 332 disposed within the collar 386, another biasing means is provided in the form of a leaf spring 402. The leaf spring 402 is attached to the upper portion of the positioning member 382 by a fastener 404 to provide a downward force upon the lever 392. The leaf spring 402 thus maintains a downward force on the transverse pin 396 greater than the upward force exerted by the coil spring 398. This allows the transverse pin 396 to contact a drill sleeve 332 disposed within the collar 386 with sufficient force to maintain the drill sleeve 332 in a substantially stationary position. A head 406 is preferably integrated with the transverse pin 396 and is positioned between the spring 398 and the lever 392 to provide an abutment surface for the lever 392 and a bearing surface for the spring 398.

The drill guide 380 also includes a guide arm 410 which is similar to the guide arm 360 set forth in the prior embodiment of the present invention. However, the guide arm 410 is contoured on its external surfaces for facilitating manipulation by hand. The contour of the guide arm 410 may be integral formations with the contour of the positioning member 382 as is shown in FIGS. 27 and 28. The guide arm 410 includes a guide region 412 having a first guide section 414 and second guide section 416 in substantially similar manner as before. These are operable to simultaneously contact the trochlear groove and the roof of the femoral intercondylar notch in a manner similar to that discussed above. The drill guide 380 also includes a third guide section in the form of an extension 418 having a longitudinal axis 420, a tip 422, a heel 424 and a stop 426, which are similar to that described above. The magnitude of the parameters a, b, Θ and Φ are all substantially the same for this embodiment of drill guide 380 as with the prior embodiment discussed above.

The method of using the drill guide of the present invention will now be described with reference to FIGS. 29–32. It will be appreciated that the drill guide of the present invention is used within an anterior cruciate ligament replacement procedure and that many steps of which are well known to those skilled in the art. Accordingly, the present discussion will focus on the steps unique to use of the drill guide of the present invention, along with other steps where desirable to maintain context or to provide better explanation. In addition, while it will be appreciated that the placement steps of the method described herein are suitable for use with various embodiments of the drill guide, reference will be made only to the embodiment of the drill guide designated by the numeral 330 for ease of explanation.

The first step of the method of the present invention involves medial portal placement. In this step, the surgeon palpates the medial and lateral edge of the patellar tendon and marks these with a pen. A medial portal is then created adjacent the medial edge of the patellar tendon. A medial portal is preferred over a traditional anteromedial portal so that the drill guide 330 will center properly within the intercondylar notch.

Figure 29:
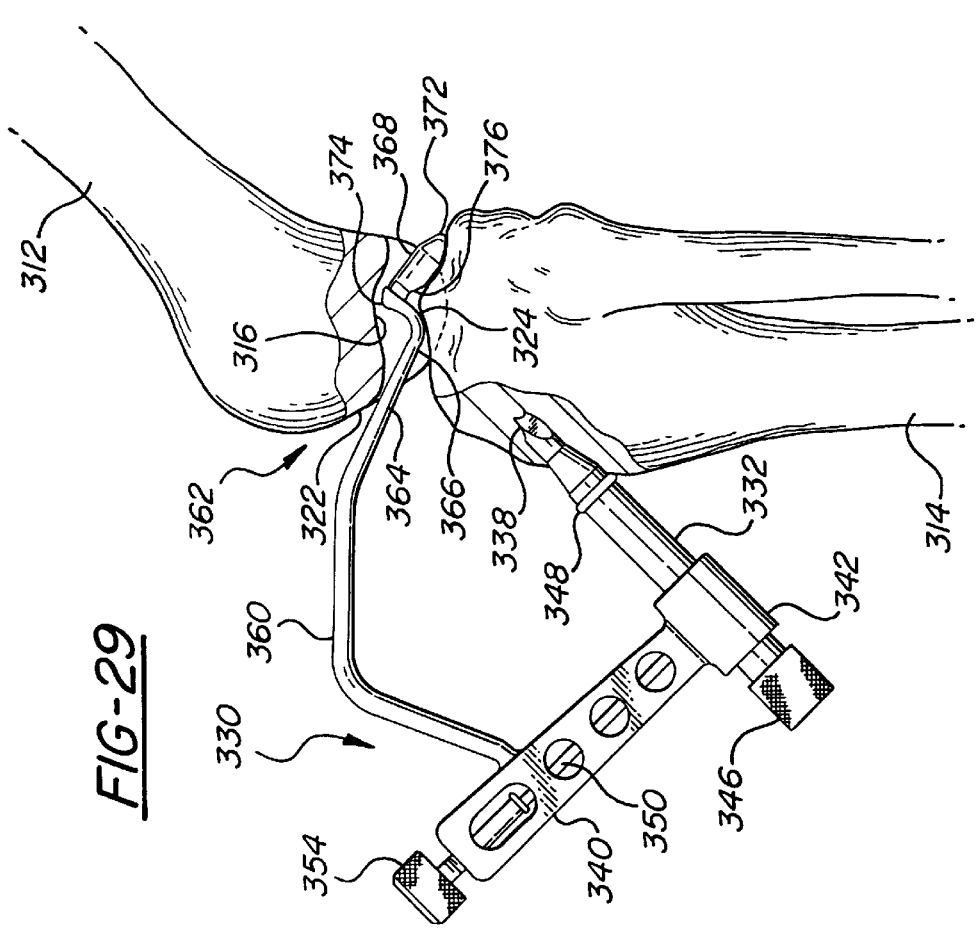
FIG. 29 is a partial cutaway view of a drill guide in a preliminary inserted position within a knee joint.

In the next step of the present invention, the drill guide 330 is inserted into the medial portal with the knee in flexion as shown in FIG. 29. The drill guide 330 is advanced so that the tip 372 of the extension 368 passes between the posterior cruciate ligament and the lateral femoral condyle. The drill guide 330 is further advanced until the heel 374 is inside the femoral intercondylar notch 316 facing the intercondylar roof.

Once the drill guide 330 is in the above position, the drill guide 330 is seated by initially extending the knee slowly while the surgeon views the relationship between the guide arm 360 and the trochlear groove 322. The movement of the knee is continued toward full extension, while manipulating the drill guide 330 to place it in the position indicated below. This may preferably be accomplished by placing the heel on a raised Mayo stand. The drill guide 330 is partially seated when the knee is fully extended while the first guide section 364 of the guide arm 360 is flush against the trochlear groove 322 with the tip 372 and heel 374 disposed within the femoral intercondylar notch 316.

Figure 30:
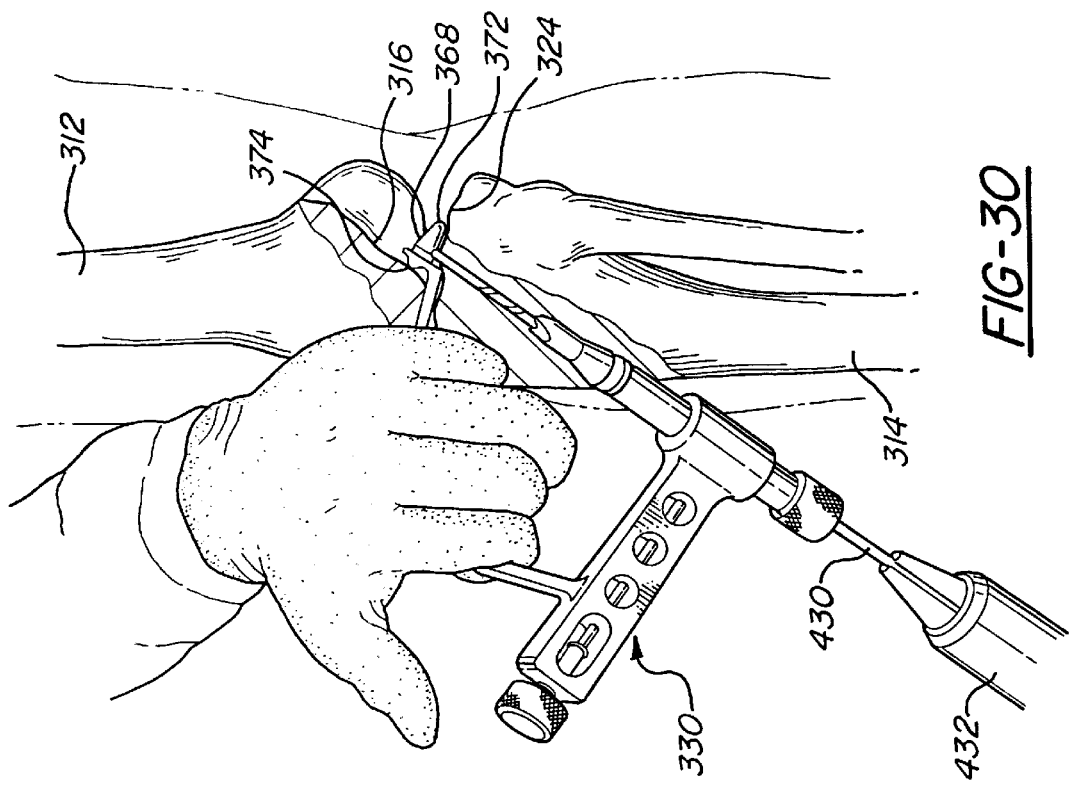
FIG. 30 is a partial cutaway view of a drill guide in an inserted position within a knee joint for guiding the drilling of a tibial tunnel.

According to the next step of the present invention, the drill guide 330 is positioned to be fully seated. This involves gently pulling the guide arm 360 in an upward direction as shown in FIG. 30 with the long and ring fingers while simultaneously hyperextending the knee passively by pushing the patella in a downward direction with the hypothenar surface of the same hand. This is continued until a resistance is felt which indicates that the drill guide 330 is aligned and will create a tibial tunnel that will be posterior and parallel to the slope of the intercondylar roof with the knee in full extension. In this configuration, the first guide section 366 contacts the trochlear groove 322 while the heel 374 contacts the roof of the femoral intercondylar notch 316 and the tip 372 contacts the tibial eminence 324 as shown in FIG. 24.

The drill sleeve 332 is then advanced forward within the collar 342 so that the tri-point tip 338 contacts the tibia 314. The thumb screw 354 is then tightened to secure the drill sleeve 332 in a substantially stationary position. In the embodiment of the drill guide represented by 380 in FIGS. 27 and 28, the lever 392 is depressed which releases the transverse pin 396 from contact with the drill sleeve. The drill sleeve can then be moved forward until it abuts the tibia, after which the lever 392 is released which secures the drill sleeve in a substantially stationary position.

In the next step of the present invention, the tibial tunnel is created using the drill guide 330. This is preferably accomplished by first utilizing the drill guide 330 to create a guide hole and subsequently using the guide hole to create a tibial tunnel. With the drill guide 330 fully seated, a drilling device, such as a 2.4 mm drill tip K-wire shown at 430 in FIG. 30, is placed through the aperture 334 of the drill sleeve 330. The K-wire 430, or other drilling device, is powered by a suitable device, such as hand drill 432, and is advanced into the tibia 314 until the K-wire 430 penetrates the subchondral bone of the tibia 314. The drill guide 330 is then disassembled and the K-wire 430 is tapped into the knee joint 1–2 cm. An arthroscope is then preferably inserted through a lateral portal to assess the placement of the drilling device. Since the position of the K-wire 430 has been customized to the patient's particular anatomy with regard to roof angle and degree of knee extension, this position will vary from one patient to another. With the knee in full extension, there should be only 2–3 mm of space between the roof of the femoral intercondylar notch 316 and the K-wire 430. Medial-laterally, the K-wire 430 should touch or be just lateral to the lateral edge of the posterior cruciate ligament at 90° of flexion, and centered within the lateral half of the femoral intercondylar notch 316 near terminal extension. Once the proper placement of the K-wire is verified, the K-wire 430 is then used to create a tibial tunnel. This is preferably accomplished by placing an appropriate sized cannulated reamer over the K-wire 430 and drilling the tibial tunnel by methods well known to those skilled in the art.

Figure 32:
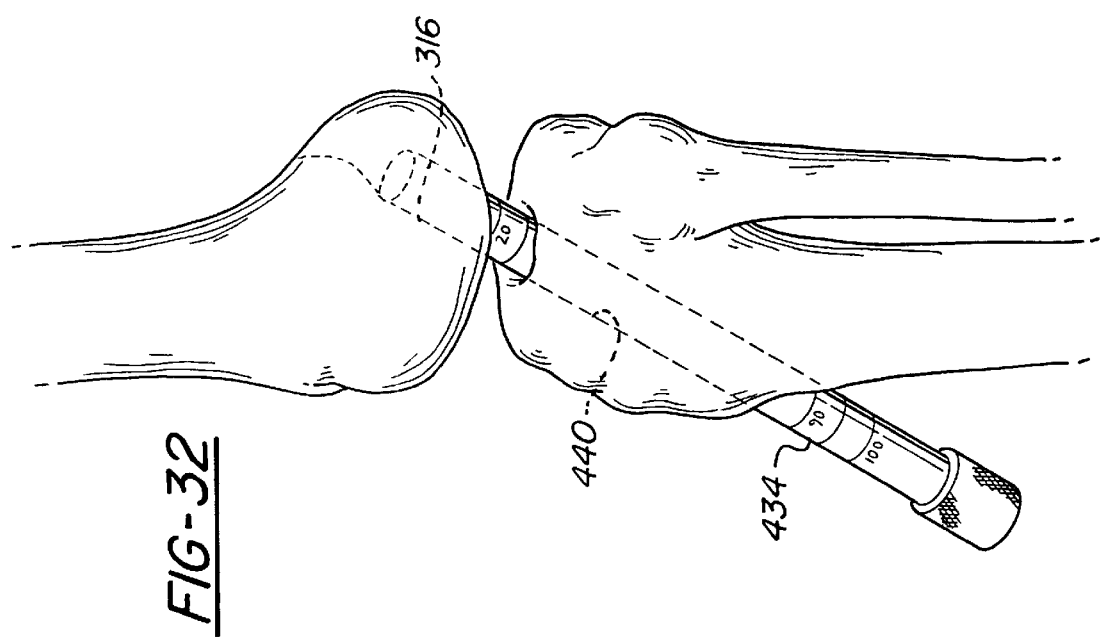
FIG. 32 is a partial cutaway view of an impingement rod inserted through a tibial tunnel and inserted into an intercondylar roof following notchplasty.
Figure 31:
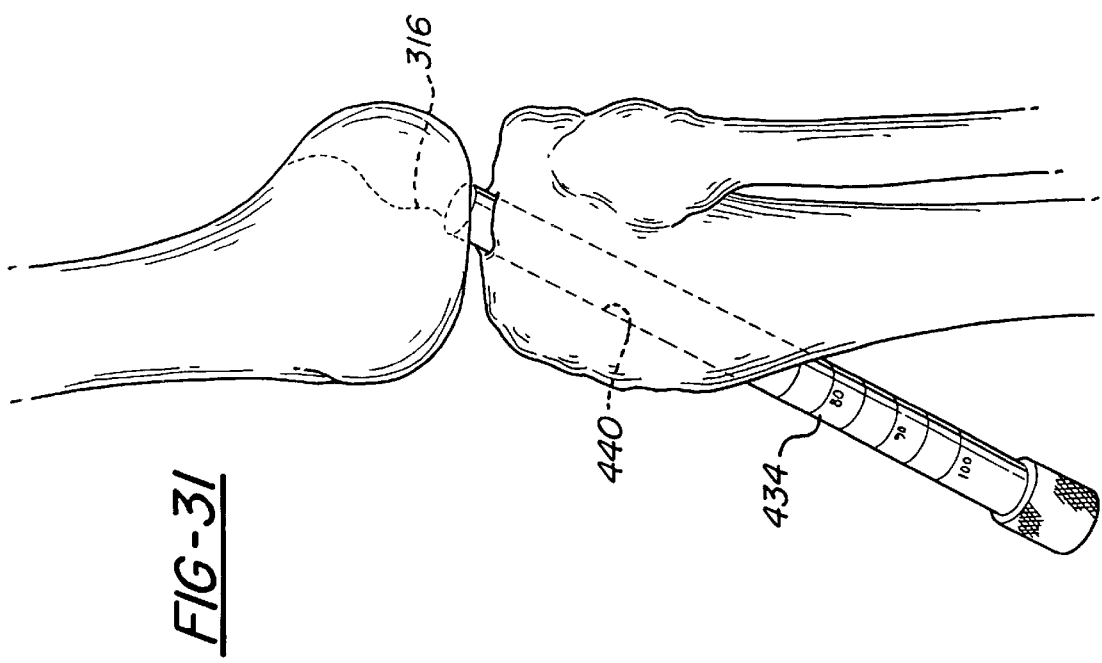
FIG. 31 is a partial cutaway view of an impingement rod inserted through a tibial tunnel and partially inserted into an intercondylar roof.

Once the tibial tunnel is formed according to the steps above, impingement of an ACL graft within the femoral intercondylar notch is assessed. The knee is placed in maximum extension and an impingement rod or sizer member of the type shown in FIG. 31 at 434, having the same diameter as the tibial tunnel, is inserted through the tibial tunnel shown at 440 and into the femoral intercondylar notch 316. If passage of the impingement rod 434 is obstructed, roof impingement exists and removal of bone within the femoral intercondylar notch 316 is necessary. A roofplasty and/or wallplasty is then performed according to methods well-known to those skilled in the art using suitable tools, such as a roof gouge and angled wall osteotome. Bone is removed from within the femoral intercondylar notch 316 until it can be estimated through the use of the impingement rod 434 that impingement will be eliminated. This is confirmed once the impingement rod 434 can be freely placed through the tibial tunnel 440 and into the femoral intercondylar notch 316 with the knee in full extension, as shown in FIG. 32. The remainder of the ACL replacement surgery is then performed using methods well-known to those skilled in the art.

Referring now to FIGS. 33–36, an alternate embodiment of the drill guide of the present invention is shown and designated by the reference numeral 500. The drill guide 500 is substantially similar to the drill guide 380 as shown in FIGS. 27 and 28. In this regard, like reference numerals will be used to identify like structures with respect to the drill guide 500. The tibial drill guide 500 includes the positioning member 382 and the guide arm 410. The guide arm 410 includes the guide region 412, the first guide region 414, the second guide region 416 and the extension 418. Extension 418 extends along the longitudinal axis 420 and includes the tip 422, the heel 424 and the stop 426. The magnitude of the parameters A, B, θ, φ are all substantially the same for this embodiment of the drill guide 500 as with the drill guides 330 and 380.

Passing through the guide arm 410 is a first guide bore 502 and a second adjacent guide bore 504. When referring to FIG. 33, the guide bore 502 angles inward to the right and the guide bore 504 angles inward to the left. Each guide bore 502 and 504 are aligned along axis 506 which is substantially perpendicular to the drilling axis 390 and positioned symmetrically about lobe 508.

Figure 34:
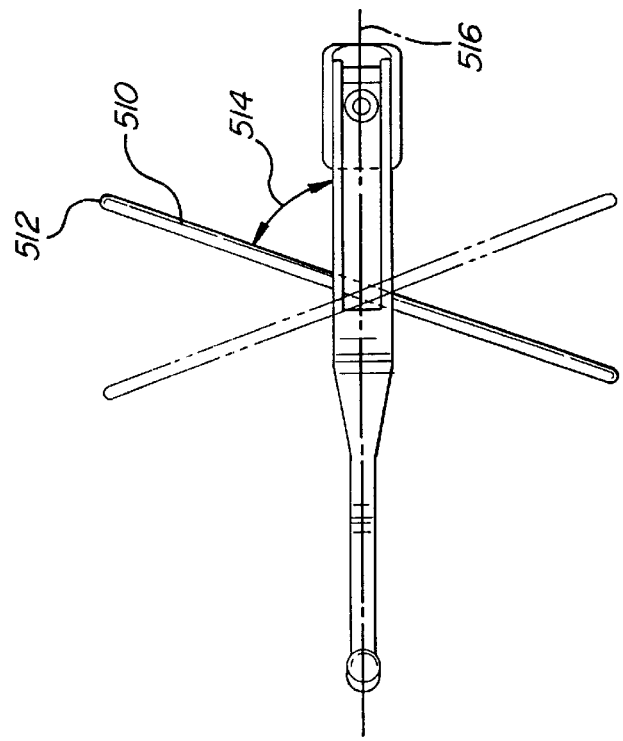
FIG. 34 is a top view of the drill guide set forth in FIG. 33 showing a guide rod for use in a right knee and a second guide rod shown in phantom for use in a left knee.
Figure 33:
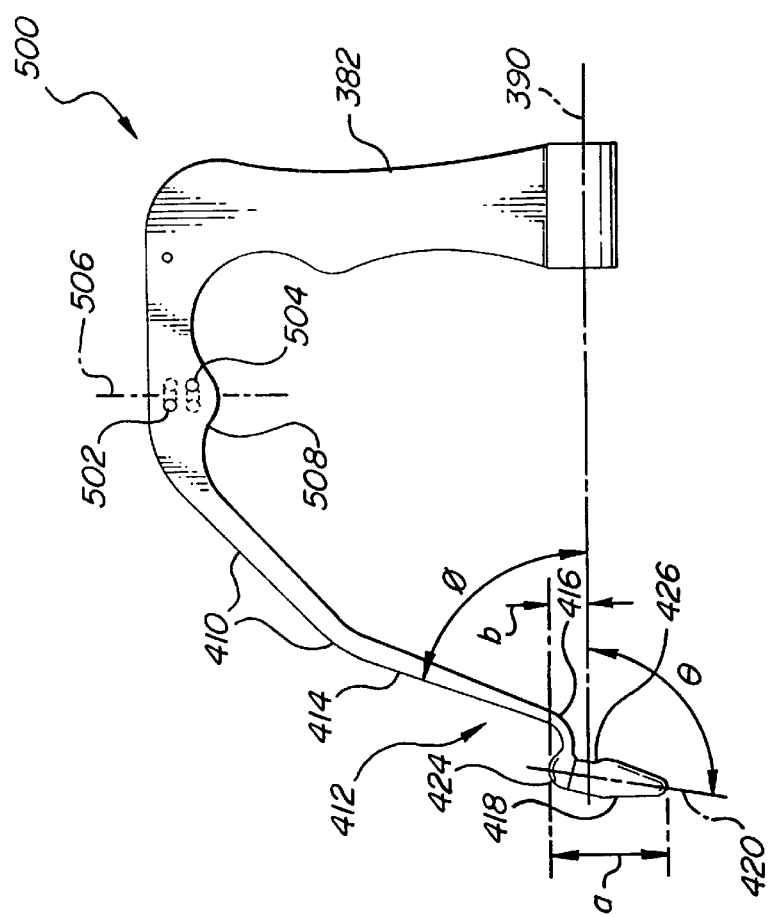
FIG. 33 is a side view of a drill guide according to the teachings of a fourth preferred embodiment of the present invention illustrating a pair of apertures extending through a guide arm.

An elongated cylindrical guide bar 510 having rounded ends 512 is operable to be slidably received within either of the guide bores 502 and 504 which are defined by the guide arm 410. The solid guide bar 510, shown in FIG. 34 is slidably inserted into guide bore 502 for use in guiding the tibial guide relative to a right knee. Should a surgeon be working with the left knee, the guide bar 510 is simply slidably received within guide bore 504, shown in phantom in FIG. 34. The guide bar 510 passes through the guide arm 410 at an angle of about seventy degrees (70°) identified by reference numeral 514, relative to axis 516. Aiming axis 516 is substantially axially aligned with drilling axis 390. The guide bar 510 is also aligned substantially perpendicular to axis 518, shown in FIG. 35. By providing the guide bar 510, the surgeon can visually align and site the guide bar 510 substantially parallel with the coronal plane to provide optimal tibial tunnel placement in the medial-lateral plane. In this regard, the tibial tunnel will be bored through the tibia at an angle of about seventy degrees (70°) relative to the coronal plane.

Figure 36:
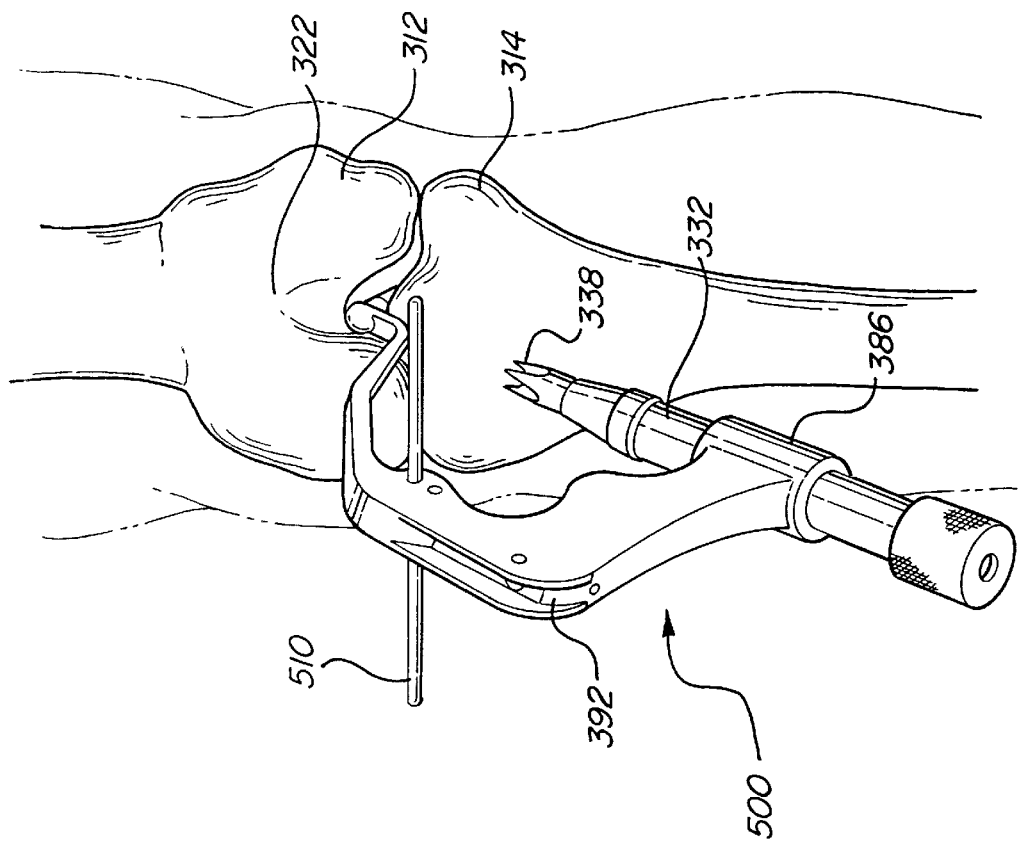
FIG. 36 is a perspective view of the drill guide set forth in FIG. 33 illustrating aligning the drill guide relative to the coronal plane.
Figure 35:
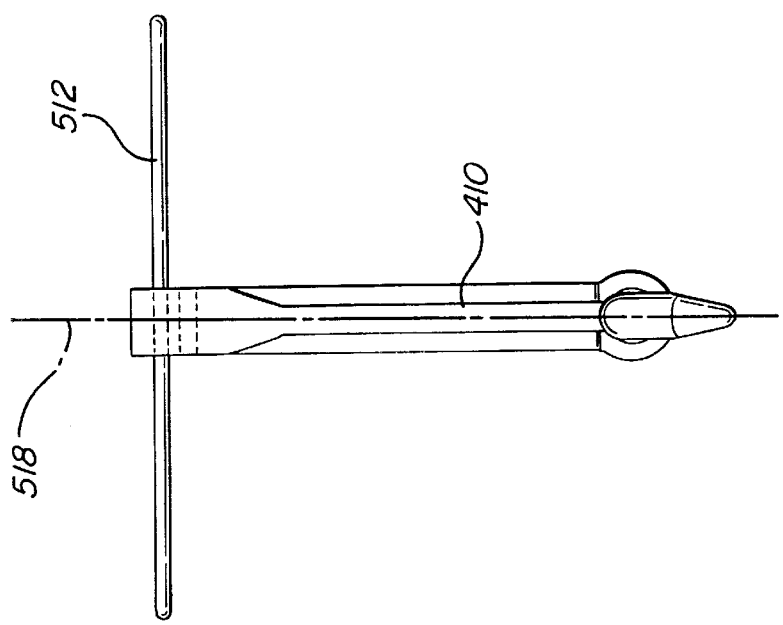
FIG. 35 is a front view of the drill guide set forth in the FIG. 33 showing the guide rod for use in the right knee being substantially perpendicular to the drill guide.

The method of using the drill guide 500 will now described with reference to FIG. 36. It will be appreciated that the drill guide 500 of the present invention is used within an anterior cruciate ligament replacement procedure and again, many steps are well known to those skilled in the art or are previously described herein. Accordingly, the present discussion will focus on the steps unique to the use of the drill guide 500 of the present invention.

The drill guide 500 is aligned relative to the femur 312 and the tibia 314 similar to that shown in FIGS. 29–30. In this regard, the drill guide 500 is advanced so that the tip 422 of the extension 418 passes between the posterior cruciate ligament and the lateral femoral condyle. The drill guide 500 is again further advanced until the heel 424 is inside the femoral intercondylar notch 316 facing the intercondylar roof. Once the drill guide 500 is in this position, the drill guide 500 is seated by extending the knee slowly while the surgeon views a relationship between the guide arm 410 and the trochlear groove 322 (see FIG. 30). Additionally, the alignment of the drilling axis 390 or axis 516 relative to the coronal plane is also aligned based upon the relative position of the guide bar 510. Here again, the guide bar 510 is preferably aligned substantially parallel to the coronal plane which is about seventy degrees (70°) offset from the coronal plane to provide optimum angular position of the tibial tunnel. This alignment occurs as the guide arm 500 gently pulls upward, as shown in FIG. 30 until the first guide section 414 contacts the trochlear groove 322, while the heel 424 contacts the roof of the femoral intercondylar notch 316 and the tip 422 contacts the tibial eminence 324, as shown in FIG. 24. For a right knee, the drill guide 500 is rotated medially toward the left knee and for the left knee, the drill guide 500 is also rotated medially toward the right knee, such that the guide bar 510 is aligned substantially parallel to the coronal plane.

Once in this position, the drill sleeve 332 is advanced forward within the collar 386 so that the tri-point tip 338 contacts the tibia 314. The lever 392 is depressed which releases the transfers pin 396 from contact with the drill sleeve 332 to enable the drill sleeve to be moved forward until it abuts the tibia 314. Once the drill sleeve 332 abuts the tibia 314, the lever 392 is released to secure the drill sleeve 332 in a substantially stationary position. The tibia tunnel is then created using the drill guide 500. In this regard, the tibial tunnel is formed as previously described, except that the tibial tunnel is now aligned to its optimal position relative to the coronal plane, via utilizing the guide bar 510, for a line of site aiming and alignment of the tibial tunnel. This alignment of the tibial tunnel relative to the coronal plane at about a seventy degree (70°) angle reduces overall stresses in the subsequently implanted graft, thereby achieving optimal repair of the anterior cruciate ligament.

While the above detailed description describes the preferred embodiment of the present invention, it should be understood that the present invention is susceptible to modification, variation and alteration without deviating from the scope and fair meaning of the subjoined claims.

What is claimed is:

1. An arthroscopic drill guide for use in drilling a tunnel in a knee joint having a femur with an intercondylar roof and a trochlear groove, and a tibia having a tibial eminence, said drill guide comprising:
   a drill sleeve defining an aperture extending along a drilling axis, said aperture operable to guide a drilling procedure;
   a guide assembly disposed in communication with said drill sleeve, said guide assembly operable to reference at least one landmark, said guide assembly defining a pair of guide bores; and
   a guide bar disposed in communication with said guide assembly and operable to be slidably received within each of said guide bores, said guide bar providing visual alignment of said drilling axis relative to the coronal plane passing through the knee joint.

2. The drill guide as defined in claim 1 wherein said guide bar is operable to be aligned relative to said drilling axis for use in drilling a tunnel in one of either a right and a left knee.

3. The drill guide as defined in claim 1 wherein said guide assembly includes a positioning member and a guide arm, said positioning member extending from said drill sleeve and operable to be gripped by a user and said guide arm extending from said positioning member and operable to reference at least one landmark.

4. The drill guide as defined in claim 3 wherein said guide bar is disposed in communication with said guide arm.

5. The drill guide as defined in claim 4 wherein said guide arm defines said pair of guide bores.

6. The drill guide as defined in claim 1 wherein said guide assembly is operable to reference at least three (3) anatomical landmarks in the knee.

7. The drill guide as defined in claim 1 wherein said guide assembly includes a guide region having a guide section operable to contact the trochlear groove and an extension having a distal tip operable to contact the tibial eminence and a bulbous shaped heel positioned opposite said distal tip operable to contact the intercondylar roof of the femur.

8. An arthroscopic drill guide for use in drilling a tunnel in a knee joint having a femur with an intercondylar roof and a trochlear groove, and a tibia having a tibial eminence, said drill guide comprising:
   a drill sleeve defining an aperture extending along a drilling axis, said aperture operable to guide a drilling procedure;
   a guide assembly disposed in communication with said drill sleeve, said guide assembly operable to reference at least one landmark; and
   a guide bar disposed in communication with said guide assembly, said guide bar providing visual alignment of said drilling axis relative to the coronal plane passing through the knee joint, wherein said guide bar is positioned at about seventy degrees (70°) relative to said drilling axis, wherein said guide bar is operable to be visually aligned substantially parallel with the coronal plane.

9. An arthroscopic drill guide for use in drilling a tunnel in a knee joint having a femur with an intercondylar roof and a trochlear groove, and a tibia having a tibial eminence, said drill guide comprising:
   a drill sleeve defining an aperture extending along a drilling axis, said aperture operable to guide a drilling procedure;
   a positioning member extending from said drill sleeve, said positioning member operable to be gripped by a user;
   a guide arm having a proximal end and a distal end, said proximal end in mechanical communication with said positioning member and said distal end including a guide region operable to reference at least one landmark in the knee; and
   a removable guide bar operable to be removably coupled to said guide arm in at least two orientations for permitting visual alignment of said drill guide relative to the coronal plane of the knee.

10. The drill guide as defined in claim 9 wherein said guide arm defines a first bore angled relative to said drilling axis and a second bore angled relative to said drilling axis, said guide bar operable to be slidably received in either of said first guide bore and said second guide bore.

11. The drill guide as defined in claim 9 wherein said guide bar is an elongated cylindrical bar.

12. The drill guide as defined in claim 9 wherein said guide bar is operable to be positioned at about seventy degrees (70°) relative to said drilling axis.

13. The drill guide as defined in claim 9 wherein said guide region includes a guide section operable to contact the trochlear groove and an extension having a distal tip operable to contact the tibial eminence and a bulbous shaped heel positioned opposite said distal tip operable to contact the intercondylar roof of the femur.

14. The drill guide as defined in claim 9 wherein said at least one landmark within the knee is an anatomical landmark.

* * * * *

UNITED STATES PATENT AND TRADEMARK OFFICE
CERTIFICATE OF CORRECTION

PATENT NO. : 6,254,604 B1
DATED : July 3, 2001
INVENTOR(S) : Stephen M. Howell

It is certified that error appears in the above-identified patent and that said Letters Patent is hereby corrected as shown below:

Column 8,
Line 50, "aoint" should be -- (joint) --.

Column 11,
Line 47, "tni-point" should be -- tri-point --.
Line 49, "tn-point" should be -- tri-point --.
Line 52, delete the comma after "the".

Column 12,
Line 22, "Uibial" should be -- tibial --.

Column 14,
Line 12, delete "30".
Line 40, delete "an" and substitute -- and -- therefor.

Column 16,
Line 63, delete "is 20" and substitute -- 20 is -- therefor.

Column 17,
Line 22, delete "20".
Line 33, delete "os10"
Line 64, delete "o10".

Column 18,
Line 62, delete "an" and substitute -- a -- therefor.

Column 19,
Line 31, delete "32" and substitute -- 332 -- therefor.

Column 21,
Line 1, delete "form" and substitute -- from -- therefor.

Column 24,
Line 40, after "now" insert -- be --.

UNITED STATES PATENT AND TRADEMARK OFFICE
CERTIFICATE OF CORRECTION

PATENT NO. : 6,254,604 B1
DATED : July 3, 2001
INVENTOR(S) : Stephen M. Howell

It is certified that error appears in the above-identified patent and that said Letters Patent is hereby corrected as shown below:

<u>Column 26,</u>
Line 12, delete "transfers" and substitute -- transfer -- therefor.

Signed and Sealed this

Thirtieth Day of July, 2002

*Attest:*

*Attesting Officer*

JAMES E. ROGAN
*Director of the United States Patent and Trademark Office*